(12) United States Patent
Graham et al.

(10) Patent No.: US 9,790,502 B2
(45) Date of Patent: *Oct. 17, 2017

(54) HBV TREATMENT

(71) Applicant: BENITEC BIOPHARMA LIMITED, Balmain, New South Wales (AU)

(72) Inventors: Michael Wayne Graham, Jindalee (AU); Peter French, Balmain (AU); York YuanYuan Zhu, Palo Alto, CA (US); YiXiang Lu, Nantong (CN); TieJun Li, Nantong (CN); YunCheng Sun, Nantong (CN); XiaoJun Tang, Nantong (CN); Li Shan, Laval (CA)

(73) Assignee: BENITEC BIOPHARMA LIMITED, Balmain, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/206,948

(22) Filed: Jul. 11, 2016

(65) Prior Publication Data

US 2017/0002356 A1    Jan. 5, 2017

Related U.S. Application Data

(63) Continuation of application No. 14/731,824, filed on Jun. 5, 2015, now Pat. No. 9,410,154, which is a continuation of application No. 13/882,124, filed as application No. PCT/CN2011/081386 on Oct. 27, 2011, now Pat. No. 9,080,174.

(30) Foreign Application Priority Data

| | | |
|---|---|---|
| Oct. 28, 2010 | (CN) | 2010 1 0521948 |
| Oct. 28, 2010 | (CN) | 2010 1 0521962 |
| Oct. 28, 2010 | (CN) | 2010 1 0521972 |
| Oct. 28, 2010 | (CN) | 2010 1 0521975 |
| Oct. 28, 2010 | (CN) | 2010 1 0521990 |
| Oct. 28, 2010 | (CN) | 2010 1 0522003 |
| Oct. 28, 2010 | (CN) | 2010 1 0522005 |

(51) Int. Cl.
   *C07H 21/04*    (2006.01)
   *C12N 15/113*   (2010.01)

(52) U.S. Cl.
   CPC ...... *C12N 15/1131* (2013.01); *C12N 2310/14* (2013.01); *C12N 2310/531* (2013.01)

(58) Field of Classification Search
   CPC .................................................. C07H 21/04
   See application file for complete search history.

(56) References Cited

U.S. PATENT DOCUMENTS

2003/0206887 A1   11/2003   Morrissey et al.
2006/0189561 A1   8/2006    Roelvink et al.

FOREIGN PATENT DOCUMENTS

| | | |
|---|---|---|
| CN | 101684478 | 3/2010 |
| CN | 101979556 | 2/2011 |

OTHER PUBLICATIONS

Grimm, et al. 2007 "Combinatorial RNAi: A winning strategy for the race against evolving targets?" Molecular Therapy 15: 878-888.
Li, Z. et al. 2009 "Inhibition of HBV replication and gene expression in vitro and in vivo with a single AAV vector delivering two shRNA molecules" BMB Reports 42: 59-64.
Romano, P.R. et al. 2006 "RNA interference-mediated prevention and therapy for hepatocellular carcinoma" Oncogene 25: 3857-3865.
Snyder, L.L. et al. 2009 "RNA Polymerase III can drive polycistronic expression of functional interfering RNAs designed to resemble microRNAs" Nucleic Acids Research 37: e127 (10 pages).
Supplemental European Search Report, in European Application No. 11 83 5635, dated Mar. 14, 2014.
Tang, Tong-Yu 2009 "Inhibition of HBV with RNAi based on microRNA" Chinese Doctoral Dissertations Full-text Database Medicine and Health Sciences, Aug. 15, 2009, year 2009, No. 8, p. E061-2.
Weinberg, M.S. et al. 2007 "Specific inhibition of HBV replication in vitro and in vivo with expressed long hairpin RNA" Molecular Therapy 15(3): 534-541.
Wu, K.-L. et al. 2005 "Inhibition of Hepatitis B virus gene expression by single and dual small interfering RNA treatment" Virus Research 112: 100-107.
Ji, et al. 2003 "Enhanced gene silencing by the application of multiple specific small interfering RNAs" FEBS Letters 552: 247-252.
Radulovich, et al. 2011 "Modified gateway system for double shRNA expression and Cre/lox based gene expression" BMC Biotechnology 11: 24 (in 9 pages).
Schuck, et al. 2004 "Generation of single and double knockdowns in polarized epithelial cells by retrovirus-mediated RNA interference" Proceedings of the National Academy of Sciences 101(14): 4912-4917.
Yu, et al. 2003 "Simultaneous inhibition of GSK3.alpha. and GSK3.beta. using hairpin siRNA expression vectors" Molecular Therapy 7(2): 228-236.

(Continued)

*Primary Examiner* — Kimberly Chong
(74) *Attorney, Agent, or Firm* — Fenwick & West LLP

(57) ABSTRACT

This invention is directed to a RNA interference (RNAi) agent and the use of that RNAi agent to treat hepatitis B infection in individuals, as well as pharmaceutical compositions containing the RNAi agents of the invention. The RNAi agents, or constructs for expressing them are utilized to inhibit expression of at least one Hepatitis B virus (HBV) gene, where the agent comprises an effector sequence complementary to or substantially complementary to a predicted sequence transcribed from a target region. In some forms of the invention, the agent has more than one effector sequence. Multiple effectors may target the same region of an HBV gene, different (possibly overlapping) regions of the same gene and/or different HBV genes.

26 Claims, 13 Drawing Sheets

(56) References Cited

OTHER PUBLICATIONS

United States Office Action, U.S. Appl. No. 14/731,824, Dec. 3, 2015, 7 pages.
United States Office Action, U.S. Appl. No. 13/882,124, Dec. 26, 2014, 7 pages.
United States Office Action, U.S. Appl. No. 13/882,124, May 29, 2014, 10 pages.

Expression cassette – general structure

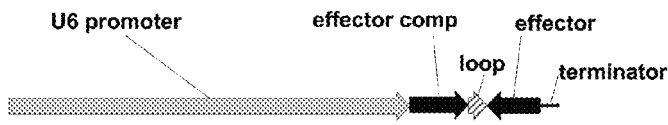

Expressed RNAi agent (hairpin structure) and single stranded, processed effector sequence (assuming 22nt phasing):

A) shRNA3 (SEQ ID NO: 36)

```
       v                          vCAA
         GAACCUUUACCCCGUUGCCCGG     \
         CUUGGAAAUGGGGCAACGGCC      G
    UU                         ^  AGA
  ^
```

5'-GGGCAACGGGGUAAAGGUUCuu-3'

(SEQ ID NO:3$_{(4\ to\ 23)}$, with nucleotides uu at the 3' end)

B) shRNA 9 (SEQ ID NO: 37)

```
       v                      CAA
         GUCAGUGGUUCGUAGGGCUUUCC  \
         UAGUCACCAAGCAUCCCGAAAGG   G
    AU                         ^ AGA
```

5'-AAAGCCCUACGAACCACUGAuu-3'

(SEQ ID NO:9$_{(4\ to\ 21)}$, with nucleotides GAuu at the 3' end)

C) shRNA12 (SEQ ID NO: 38)

```
                              vCAA
         GAUUCCUAUGGGAGUGGGCCUCA   \
         UUAAGGAUACCCUCACCCGGAGU    G
    ^                          ^ AGA
```

5'-AGGCCCACUCCCAUAGGAAUU-3'

(SEQ ID NO:12$_{(1\ to\ 19)}$, with 5' nucleotides AG)

Figure 6

D) shRNA 13 (SEQ ID NO: 39)

```
                          vCAA
       GCCAAACUCUGCAAGAUCCCAGA    \
       UGGUUUGAGACGUUCUAGGGUCU     G
    AU                         A AGA
```

5'-UGGGAUCUUGCAGAGUUUGGUu-3'

(SEQ ID NO:13$_{(1\ to\ 18)}$, with nucleotides UG at the 5' end and Uu at the 3' end)

E) shRNA 23 (SEQ ID NO: 40)

```
                          vCAA
       GCUCUGUUGUCCUCUCCCGCAAA    \
       UGAGACAACAGGAGAGGGCGUUU     G
    AU                         A AGA
```

5'-UGCGGGAGAGGACAACAGAGUu-3'

(SEQ ID NO:23, with nucleotide u at the 3')

Figure 6 continued

Expression cassette

Expressed RNAi agents

SEQ ID NO: 41        SEQ ID NO: 42        SEQ ID NO: 43

Theoretical processed effector sequence (assuming 22nt phasing)

effector 1    5'-AA<u>GAUUGACGAUAAGGGAGA</u>UU-3' (SEQ ID NO $1_{(1-18)}$ with AA at 5' & UU at 3' ends)

effector 4    5'-<u>UAUUUGCGGGAGAGGACAAC</u>UU-3' (SEQ ID NO $4_{(1-20)}$ with UU at 3' end)

effector 6    5'-<u>AAGGCCUCCGUGCGGUGGGG</u>UU-3' (SEQ ID NO: $6_{(1-20)}$ with UU at 3' end)

Expression cassette

Expressed RNAi agent: SEQ ID NO: 44

Theoretical processed effector sequence (assuming 22nt phasing)

effector 1    5'-AAGAUUGACGAUAAGGGAGAug-3'    (SEQ ID NO 1₍₁₋₁₈₎ with AA at 5' & ug* at 3')

effector 4    5'-UAUUUGCGGGAGAGGACAACUG-3'    (SEQ ID NO 4₍₁₋₂₀₎ with UG at 3' end)

effector 6    5'-AAGGCCUCCGUGCGGUGGGGUG-3'    (SEQ ID NO 6₍₁₋₂₀₎ with UG at 3')

*no homology to HBV

Expression cassette

Expressed RNAi agent: SEQ ID NO: 45

Theoretical processed effector sequence (assuming 22nt phasing)

effector 4   5'-UAUUUGCGGGAGAGGACAACAG-3' (SEQ ID NO $4_{(1-22)}$)

effector 6   5'-AAGGCCUCCGUGCGGUGGGGUG-3' (SEQ ID NO: 6 UG at 3' end)

effector 1   5'-AAGAUUGACGAUAAGGGAGAUU-3' (SEQ ID NO: 1 with AA at 5' and UU at 3')

HBV TREATMENT

CROSS REFERENCE TO RELATED APPLICATIONS

This application is a Continuation of U.S. patent application Ser. No. 14/731,824, filed Jun. 5, 2015, which is a Continuation of U.S. patent application Ser. No. 13/882,124, filed May 23, 2013, (now U.S. Pat. No. 9,080,174), which is the National Stage of International Patent Application of PCT/CN2011/081386, filed Oct. 27, 2011, which claims the benefit of Chinese Patent Application Serial Nos. 201010521962.3, filed Oct. 28, 2010, 201010521972.7, filed Oct. 28, 2010, 201010521990.5, filed Oct. 28, 2010, 201010522003.3, filed Oct. 28, 2010, 201010521948.3, filed Oct. 28, 2010, 201010521975.0, filed Oct. 28, 2010, and 201010522005.2, filed Oct. 28, 2010, each of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Jun. 29, 2016, is named 34356US_CRF_sequencelisting.txt and is 2.94 bytes in size.

FIELD OF THE INVENTION

This invention is directed to an RNA interference (RNAi) agent and the use of that RNAi agent to treat hepatitis B infection in individuals, as well as pharmaceutical compositions containing the RNAi agents of the invention.

BACKGROUND OF THE INVENTION

Hepatitis is a general term meaning 'inflammation of the liver' and has a number of causes. Viral causes are among the most common, and may be caused by hepatitis A, B, C, D or E virus. Hepatitis B virus (HBV) in particular is a serious and common infectious disease of the liver, affecting millions of people throughout the world.

HBV is a hepatotrophic DNA virus belonging to the Hepadnaviridae. The full-length of the viral genome is about 3.2 kb, and it has four open reading frames (ORFs) including surface antigen (the "S gene"), core antigen (the "C gene"), DNA polymerase (the "P gene") and a gene of undetermined function referred to as the "X gene".

More than 2,000 million people alive today have been infected with HBV at some time in their lives and of these about 350 million remain chronically infected and become carriers of the virus. HBV infection can cause acute and chronic type B hepatitis, and may eventually lead to the development of chronic hepatic insufficiency, cirrhosis, and hepatocellular carcinoma. In addition, HBV carriers can transmit the disease for many years.

HBV is transmitted by percutaneous or parenteral contact with infected bodily fluids or blood. The most common route of infection is via vertical transmission from mother to her baby, and in adults through sexual intercourse or shared intravenous needles or ear-piercing equipment. Many cases of acute HBV infection occur however without a traceable route of infection.

Persons with chronic HBV infection ("carriers"—worldwide about 350-400 million people) have a 12-300× higher risk of developing hepatocellular carcinoma than non-carriers and globally HBV causes 60-80% of the world's primary liver cancers. Every year about 25% of the over 4 million acute clinical cases (i.e. 1 million people worldwide) die from chronic active hepatitis, cirrhosis or HBV-induced liver cancer. As a consequence, HBV ranks second only to tobacco as a known human carcinogen.

Although vaccines against HBV has been widely used for several decades, the HBV prevalence rate in the population still remains high. Current therapies for chronic HBV infection have only limited inhibitory effects on viral gene expression and replication in the majority of chronically infected patients. Lamivudine for example suppresses HBV replication in carriers, but the effect is reversible if therapy is stopped. Moreover, a major limitation of chronic Lamivudine therapy is the development of viral resistance, which typically develops after 6 months of treatment. Resistance is usually associated with mutations in the highly conserved catalytic region of the HBV polymerase gene.

For these reasons, there remains a need for a new therapeutic agent to treat HBV infection. This invention is directed to an RNA interference (RNAi) agent and the use of that RNAi agent to treat hepatitis B infection in individuals.

The RNAi pathway is initiated by the enzyme Dicer, which cleaves double-stranded RNA (dsRNA) molecules into short fragments (commonly referred to as siRNAs) of ~20-25 nucleotides. One of the two strands of each fragment, known as the guide strand or active strand, is then incorporated into the RNA-induced silencing complex (RISC) through binding to a member of the argonaute protein family. After integration into the RISC, the guide strand base-pairs with its target mRNA and is thought to either inhibit a target by inhibiting translation (by stalling the translational machinery) and/or inducing cleavage of the mRNA, thereby preventing it from being used as a translation template.

While the fragments produced by Dicer are double-stranded, only the guide strand, directs gene silencing. The other anti-guide strand referred to more commonly as a passenger strand, carrier strand or * strand is frequently degraded during RISC activation (Gregory R, Chendrimada T, Cooch N, Shiekhattar R (2005). "Human RISC couples microRNA biogenesis and posttranscriptional gene silencing". Cell 123 (4): 631-40). RISC assembly is thought to be governed by an enzyme that selects which strand of a dsRNA Dicer product is loaded into RISC. This strand is usually the one whose 5' end is less tightly paired to its complement, and there also appears to be a clear bias for A, and to a lesser extent U, at the 5' position to facilitate binding to some argonaute proteins (Schwarz D S, Hutvágner G, Du T, Xu Z, Aronin N, Zamore P D (2003). "Asymmetry in the assembly of the RNAi enzyme complex". Cell 115 (2): Frank F, Sonenberg N, Nagar (2010) "Structural basis for 5'-nucleotide base-specific recognition of guide RNA by human AGO2". Nature. 465 (7299):818-22).

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

It has been discovered by the current inventors that unique sequences within the Hepatitis B Virus (HBV) genome may be targeted to inhibit the virus. By targeting specific regions of one or more genes, the expression of those genes is inhibited, effectively "silencing" the gene. This presents a new opportunity to target HBV expression in cells to treat HBV infection.

In one aspect of the invention, there is provided a DNA-directed RNA interference (ddRNAi) agent (being an RNA molecule), and an expression cassette or construct to express that agent in a cell (including in vivo), for inhibiting expression of at least one Hepatitis B virus (HBV) gene, where the agent comprises an effector sequence (described further below) of at least 17 nucleotides in length complementary to or substantially complementary to a predicted sequence transcribed from a target region, the target region being selected from the group consisting of any 10 or more contiguous nucleotides within a sequence from any one of SEQ ID NOS: 1-19. In an alternative embodiment, the target region is a sequence selected from the group consisting of any 10 or more contiguous nucleotides within a sequence from any one of SEQ ID NOS: 20-27.

The effector sequence is directed to a target region of a target RNA sequence, wherein the target sequence is a transcript of a target gene. Thus the effector sequence is 'directed to' a target region by being sufficiently complementary in sequence to a transcript from a target gene containing the target region. An RNAi agent, such as a ddRNAi agent, having a double-stranded portion containing the effector sequence, can therefore "inhibit expression of a target gene sequence" by virtue of the target gene sequence containing the target region. Accordingly, within a cell infected with HBV, the RNAi agent is capable of inhibiting expression of a target gene sequence because the sequence of the effector (as 'effector' is defined below) is substantially complementary to (at least) a region of the predicted mRNA target sequence of the target gene. This can be illustrated with the following short sequence:

5'ATTGCG3'—DNA target sequence of gene
5'AUUGCG3'—mRNA target region/sequence from transcription of the gene
3'UAACGC5'—effector sequence—which is substantially complementary to a region of the predicted mRNA target sequence.

Typically, a target region is a region of an mRNA of a gene that is intended to be silenced or to have its expression (at the level of transcription or translation) reduced.

The agent is designed so that it also comprises an effector complement sequence, ie a sequence that is substantially complementary to the effector sequence such that it will tend to anneal so as to form a double stranded RNA segment—the degree of complementarity required is more particularly explained further below. Moreover, usually one end of the double stranded segment will be linked by a loop sequence so as to form a 'hairpin' shaped structure. This is also know as an 'interrupted inverted repeat' structure, as the DNA encoding such an RNA sequence contains an inverted repeat of the region of the target gene that is transcribed to the effector sequence, interrupted by a stuffer or spacer sequence encoding the loop.

In some forms of the invention, the agent has more than one effector sequence. Multiple effectors may target the same region of an HBV gene, different (possibly overlapping) regions of the same gene and/or different HBV genes. RNAi agents such as ddRNAi agents, can contain 2 or 3 different effector sequences. As explained above, the ddRNAi agent comprises an effector complement sequence for each effector sequence, thus forming effector-effector complement pairs (ie a first effector-first effector complement pair, a second effector-second effector complement pair, etc). These pairs may be, but need not be, contiguous to one another, as long as the RNAi agent can fold so as to permit each pair to anneal. Various other considerations suggest one order or another of the effectors and effector complements along the length of the RNAi agent. Thus, embodiments of the invention include one or more of the following:

ddRNAi agent comprising, in a 5' to 3' direction, a first effector sequence; a second effector sequence; second effector complement sequence; and a first effector complement sequence;

a ddRNAi agent comprising, in a 5' to 3' direction, a first effector sequence; a second effector sequence; a third effector sequence; a third effector complement sequence; a second effector complement sequence; and a first effector complement sequence;

a ddRNAi agent comprising, in a 5' to 3' direction, a first effector; a first effector complement sequence; a second effector sequence; and a second effector complement sequence;

a ddRNAi agent comprising, in a 5' to 3' direction, a first effector sequence; a first effector complement sequence; a second effector sequence; a second effector complement sequence; a third effector sequence; and a third effector complement sequence;

a ddRNAi agent comprising, in a 5' to 3' direction, a first effector sequence; a second effector sequence; a sequence of 2 to 100 non-self-complementary nucleotides; a second effector complement sequence; and a first effector complement sequence;

a ddRNAi agent comprising, in a 5' to 3' direction, a first effector sequence; a sequence of 2 to 100 non-self-complementary nucleotides; a first effector complement sequence; a second effector sequence; a sequence of 2 to 100 non-self-complementary nucleotides; and a second effector complement sequence.

As would be understood by one skilled in the art, and as illustrated in the Figures, any particular effector sequence may be swapped in position with its complement in the agent. In particular forms of each of the embodiments described above, each effector sequence is at least 17 nucleotides in length and comprises a nucleotide sequence selected from the group consisting of any 10 or more contiguous nucleotides from a sequence from any one of SEQ ID NOS: 1-19 or SEQ ID NOS: 20-27. The effector sequences may all be the same, or may all be different, or may be a combination, eg 2 effector sequences of at least 10 contiguous nucleotides of SEQ ID NO: 1 and one effector sequence of at least 10 contiguous nucleotides of SEQ ID NO: 4.

Preferably, the effector sequence is selected from the group consisting of any contiguous 11, 12, 13, 14, 15 or 16 nucleotides within any one of SEQ ID NOS: 1-19 or SEQ ID NOS: 20-27, and most preferably 17 or more contiguous nucleotides within any one of SEQ ID NOS: 1-19 or SEQ ID NOS: 20-27. Typically, the effector complement will be the same length, or about the same length (ie ±15% nucleotide length) as its corresponding effector sequence.

In alternative embodiments, the dsRNA is comprised of 2 separate RNA strands that are annealed to form a duplex. ddRNAi agents may be expressed from a DNA expression cassette inserted into any suitable vector or ddRNAi construct. Accordingly, in aspects of the invention there is provided a ddRNAi expression cassettes comprising:

one or more promoter sequences
one or more DNA sequences, preferably being sequences that encode for any 10 or more and preferably any 17 or more contiguous nucleotides within a sequence from any one of SEQ ID NOS: 1-19 or SEQ ID NOS: 20-27,
one or more DNA sequences that encode for one or more effector complement sequences;
one or more terminator sequences
and optionally
one or more DNA sequences that encode for loop sequences; and
one or more enhancer sequences.

In some embodiments, one promoter is operably linked to multiple effector-encoding regions such that it can drive expression of them, whereas in other embodiments, each effector-encoding region is operably linked to its own promoter. In constructs where there are multiple promoters, these may be all the same or different. Preferred promoters are U6 and H1.

There is also provided ddRNAi expression constructs, into which the ddRNAi expression cassettes are inserted for expression. In addition, when the vector backbone of the construct is compatible with a delivery system, the ddRNAi expression constructs are also delivery constructs.

The invention also provides for siRNA agents that comprise a sequence of at least 17 nucleotides in length selected from the group consisting of any 10 or more contiguous nucleotides within a sequence from any one of SEQ ID NOS: 1-19 or SEQ ID NOS: 20-27 and a sequence complement with which the sequence forms a duplex, and that are capable of inhibiting expression of an HBV gene.

The invention also provides for methods of treatment of acute or chronic HBV infection in a subject, the reduction of HBV viral load in a subject, the reduction of the severity of symptoms associated with HBV infection in a subject, and the reduction of the infectivity of HBV, comprising administering a therapeutically effective amount of a ddRNAi construct, ddRNAi agent or siRNA agent of the invention wherein the ddRNAi construct, ddRNAi agent or siRNA agent inhibits expression of one or more target sequences in a Hepatitis B virus (HBV) gene, preferably at least the polymerase gene of HBV.

There is also provided a pharmaceutical composition comprising a ddRNAi agent, a ddRNAi expression cassette, a ddRNAi construct or a siRNA agent of the invention and a pharmaceutically acceptable carrier or diluent.

BRIEF DESCRIPTION OF THE DRAWINGS/FIGURES

FIG. 1A-F illustrates some of the ddRNAi agent structures of the invention.

Figure 4:
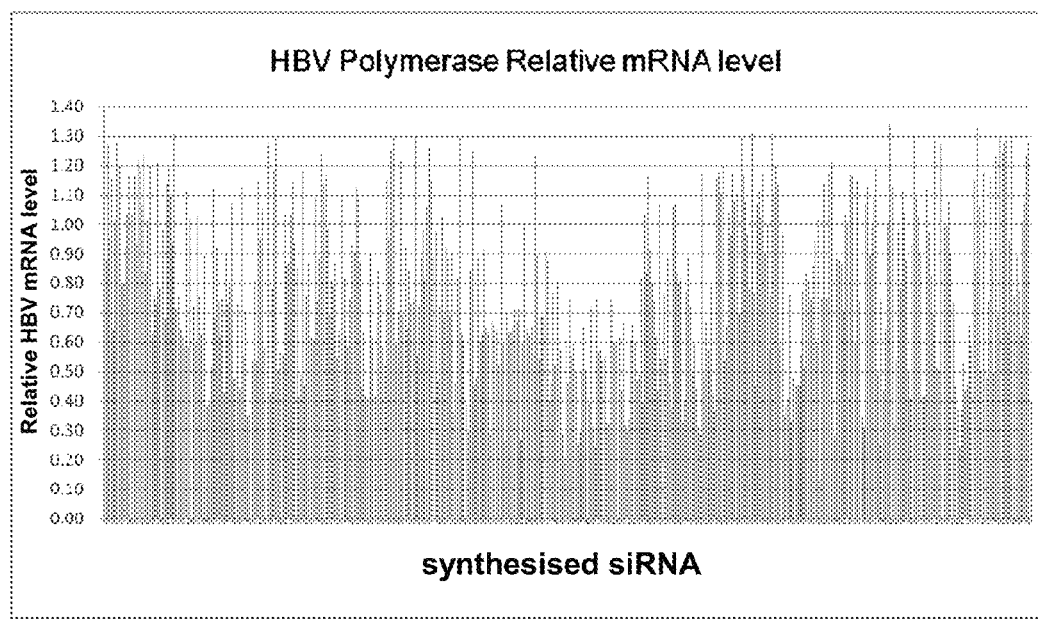
FIG. 4 is the results of the HBV polymerase inhibition screen with 501 siRNA sequences derived from the EsT library.
Figures 5A, 5B:
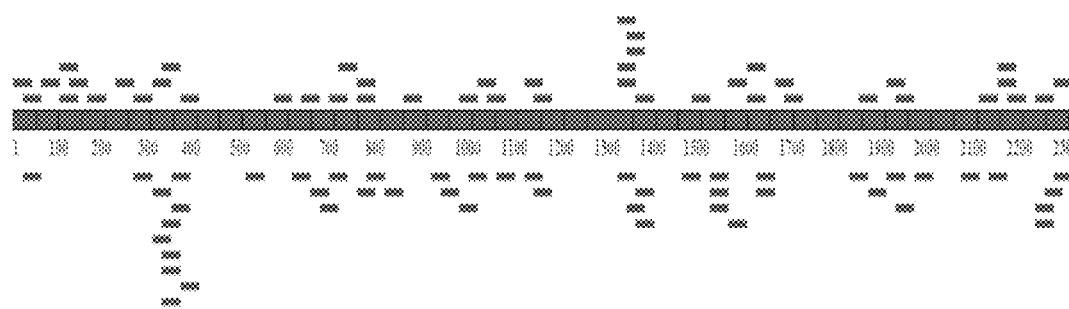

FIG. 5A is an illustration of the distribution of the top 100 most effective siRNA sequences (as identified in the large scale screen in FIG. 4) along the HBV polymerase gene. FIG. 5B illustrates how any given sequence can be mapped to the HBV polymerase gene. Shown are the areas on which SEQ ID NOS: 1 to 3 are based.

FIG. 6 is a schematic of 5 individual expression cassettes and RNAi agents encoded by them, together with the effector sequence after processing by Dicer. The expression cassettes are based on SEQ ID NO:3, 9, 12, 13 and 23.

Figure 7A:
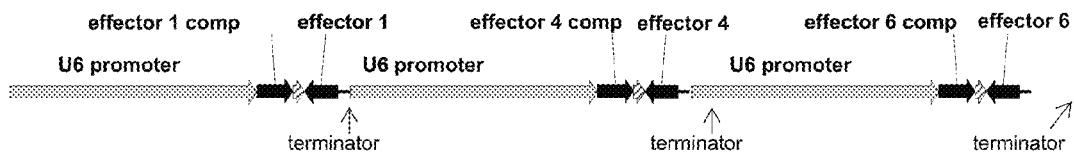
Figure 7A:
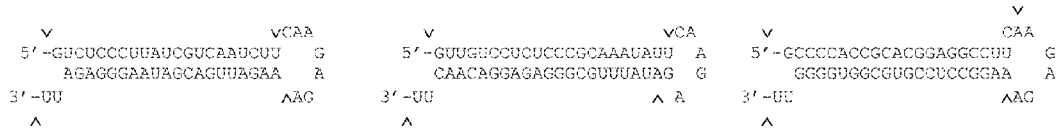

FIG. 7A is a schematic of a multiple effector sequence expression cassette containing effector sequences each operably linked to separate promoter and terminator sequences to express individual RNAi agents in the form of a short hairpin RNAi (shRNAi) agent.

Figure 7B:
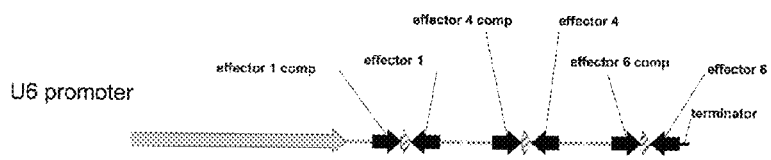
Figure 7B:
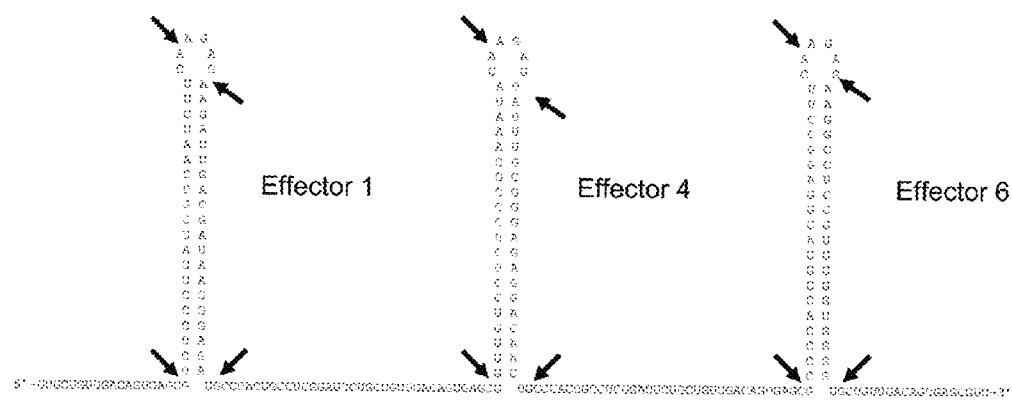

FIG. 7B is a schematic of a multiple effector sequence expression cassette containing a first effector sequence operably linked to a promoter, and a third effector sequence operably linked to a terminator such that a single multiple stem loop RNAi agent is expressed. The expression cassettes are based on SEQ ID NO:1, SEQ ID NO:4, and SEQ ID NO:6.

Figure 8:
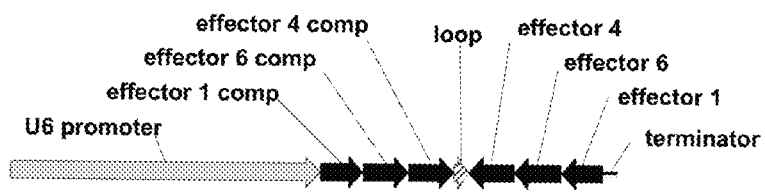
Figure 8:
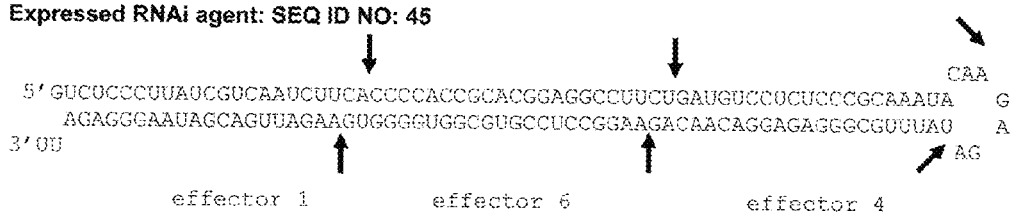

FIG. 8 is a schematic of a multiple effector sequence expression cassette based on SEQ ID NOS: 1, 4 and 6, which gives rise to a single, long hairpin RNAi agent.

Figure 9:
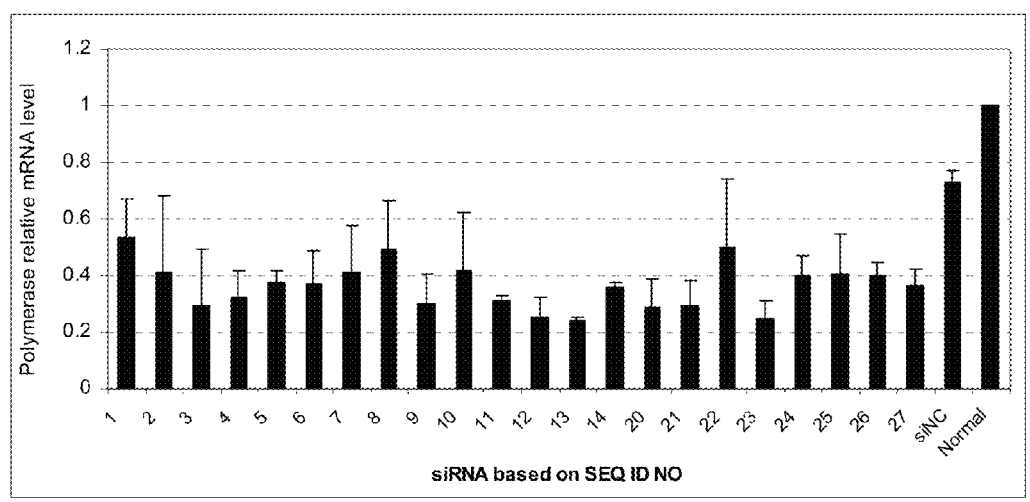

FIG. 9 illustrates the gene knockdown efficiency of SEQ ID NOS: 1 to 14 and 20 to 27 following transfection into HepG2 2.2.15 cells. Knockdown efficiency was determined by qRT-PCR analysis of polymerase gene mRNA. siNC is a negative control, being a siRNA with no known target sequences in HBV; Normal is the polymerase mRNA level in untransfected cells, standardised to a level of 1.

Figure 10A:
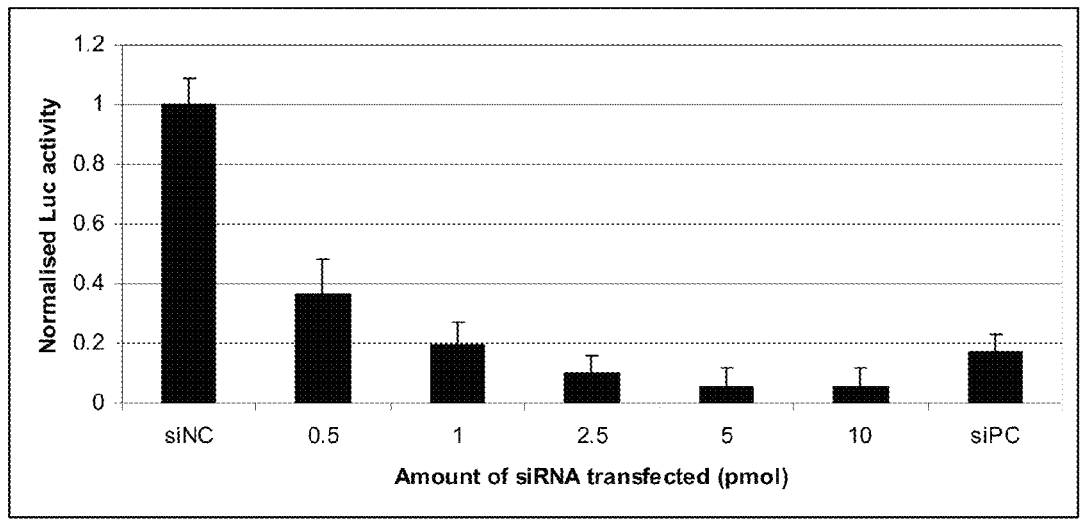
Figure 10B:
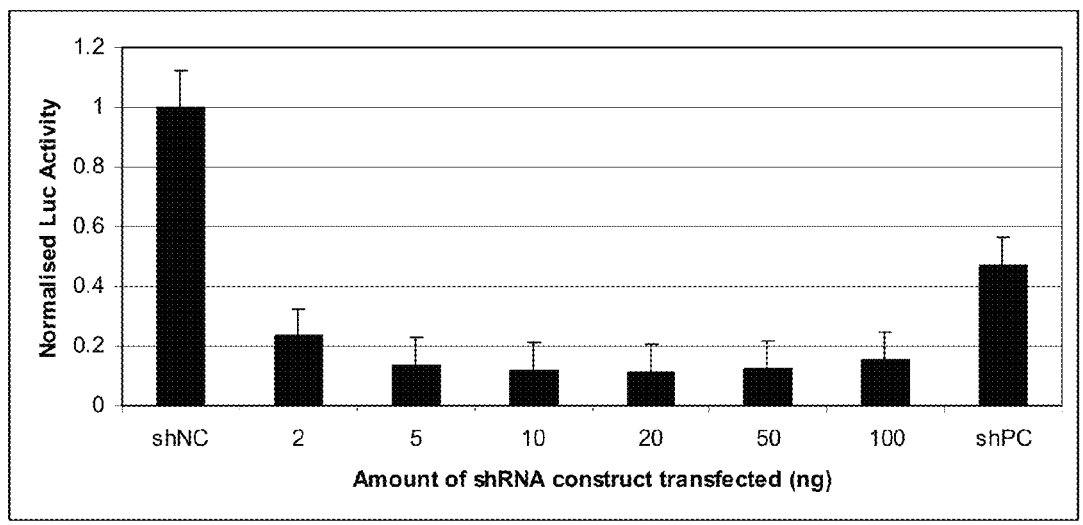

FIGS. 10A and 10B show luciferase activities (+/−SD; n=4) in cells transfected with varying quantities of chemically synthesised siRNA23 (A) or shRNA23 expression constructs (B) targeting pGL3-23 using the conditions listed in Tables 3 and 4. In FIG. 10A, siNC was used both as a negative control and to adjust total quantities of siRNAs added to cells to avoid potential artifacts due to unequal transfection; siRNA GL3 was used as a positive control, such that it is an siRNA targeted to the luciferase gene. In FIG. 10B, pUC57 was used both as a negative control and to adjust total quantities of plasmid DNAs added to cells to avoid potential artifacts due to unequal transfection. A plasmid expressing a luciferase shRNA based on GL3 siRNA was used as a positive control.

DETAILED DESCRIPTION OF THE EMBODIMENTS

Definitions

As used herein, except where the context requires otherwise, the term "comprise" and variations of the term, such as "comprising", "comprises" and "comprised", are not intended to exclude further additives, components, integers or steps.

The term "RNA interference" or "RNAi" refers generally to a RNA dependent gene silencing process that is initiated by double stranded RNA (dsRNA) molecules in a cell's cytoplasm. The dsRNA reduces the expression of a target nucleic acid sequence, which may be a DNA whose RNA expression products are reduced, or an RNA, with which the dsRNA molecule shares substantial or total homology.

By "double stranded RNA" or "dsRNA" it is meant a double stranded RNA molecule that is capable of inhibiting expression of a target nucleic acid sequence with which it shares homology. In some embodiments the dsRNA is a hairpin or stem loop structure, with a duplex region optionally linked by at least 1 nucleotide, and is referred to as a "hairpin RNA" or "short hairpin RNAi agent" or "shRNA". The duplex is formed between an effector sequence and a sequence complementary to the effector sequence herein referred to as an "effector complement". Typically, the effector complement will be the same length as its corresponding effector sequence. As will be explained below, the effector sequence is complementary to the target nucleic acid sequence.

An "effector sequence" is the nucleotide sequence that, when part of the RISC complex, binds to the HBV target nucleotide sequence, thereby targeting that sequence for destruction by the cell. It is analogous to the "guide" strand discussed in the background section. The effector sequence is 'directed to' a target region by being complementary or substantially complementary in sequence to the transcript from the target region such that an RNA agent having a double stranded portion containing the effector sequence inhibits expression of the target gene sequence.

The "effector complement", which is analogous to the passenger strand discussed in the background is of sufficient complementary to the effector such that is anneals to the effector sequence. It is likely that the effector complement will be of a similar sequence to the target gene sequence, but does not necessarily have to be.

The term "RNAi agent" refers to a dsRNA sequence that elicits RNAi. This term may be used interchangeably with "small interfering RNAs" (siRNA agents) and small hairpin RNA (shRNAi or hpRNAi agents).

The double stranded or duplex region of the RNAi agent is at least 17 base pairs long, and usually in the range of 17 to 30 base pairs. RNAi agents can be synthesized chemically or enzymatically outside of cells and subsequently delivered to cells or can be expressed in vivo by an appropriate vector in cells (see, e.g., U.S. Pat. No. 6,573,099, WO 2004/106517 and WO99/49029, all of which are incorporated herein by reference).

The term "DNA-directed RNAi agent" or "ddRNAi agent" refers to an RNAi agent that is transcribed from a DNA expression cassette ("ddRNAi expression cassette"). The ddRNAi agent transcribed from the expression cassette may be transcribed as a single RNA that is capable of self-annealing into a hairpin structure with a duplex region linked by at least 2 nucleotides, or as a single RNA with multiple shRNA domains or as multiple transcripts each capable of folding as a single shRNA.

The ddRNAi expression cassette can be ligated into vectors referred to as ddRNAi vectors or ddRNAi constructs. The vectors may provide sequences specifying transcription of the ddRNAi expression cassette in vivo or in vitro. The vector may additionally serve as the delivery vehicle for the ddRNAi expression cassette. Viral based vectors for example will generate a ddRNAi construct that is useful for expression of the ddRNAi expression cassette as well as being compatible with viral delivery.

A cell has been "transformed", "transduced" or "transfected" by an exogenous or heterologous nucleic acid or vector when such nucleic acid has been introduced into the cell. The transforming DNA may or may not be integrated (covalently linked) into the genome of the cell. With respect to eukaryotic cells, a stably transformed cell is one in which the transforming DNA has become integrated into a host cell chromosome or is maintained extra-chromosomally (episomally) so that the transforming DNA is inherited by daughter cells during cell replication. In non-replicating, differentiated cells the transforming DNA may persist as an episome.

"Gene expression" can be a reference to either or both transcription or translation.

"Inhibition of expression" refers to the absence or observable decrease in the level of protein and/or mRNA product from the target gene. The inhibition does not have to be absolute, but may be partial inhibition sufficient for there to a detectable or observable change as a result of the administration of a RNAi or ddRNAi agent or siRNA agent or ddRNAi construct of the invention. Inhibition may be measured by determining a decrease in the level of mRNA and/or protein product from a target nucleic acid relative to a cell lacking the ddRNAi agent or construct, and may be as little as 1%, 5% or 10%, or may be absolute ie 100% inhibition. The effects of inhibition may be determined by examination of the outward properties ie quantitative and/or qualitative phenotype of the cell or organism, and may also include an assessment of the viral load following administration of a ddRNAi agent or construct of the invention.

As used herein, "a quantitative phenotypic trait" refers to a trait associated with the molecular expression of a nucleic acid in a host cell and may thus include the quantity of RNA molecules transcribed or replicated, the quantity of post-transcriptionally modified RNA molecules, the quantity of translated peptides or proteins, or the activity of such peptides or proteins.

A reduction of phenotypic expression of a nucleic acid where the phenotype is a qualitative trait means that in the presence of the RNAi agent of the invention, the phenotypic trait switches to a different state when compared to a situation in which the RNAi agent is absent. A reduction of phenotypic expression of a nucleic acid may thus be measured as a reduction in steady state levels of (part of) that nucleic acid, a reduction in translation of (part of) that nucleic acid or a reduction in the effect the presence of the transcribed RNA(s) or translated polypeptide(s) have on the eukaryotic cell or the organism, and will ultimately lead to altered phenotypic traits. It is clear that the reduction in phenotypic expression of a nucleic acid of interest may be accompanied by or correlated to an observable change in phenotype. The assessment may be by way of biochemical techniques such as Northern hybridisation, quantitative real-time PCR assays, gene expression assays, antibody binding, ELISA, RIA, western blotting and other assays and techniques known in the art.

"Target nucleic acids" may be either RNA or DNA, whose transcription products are targeted, coding or non-coding sequence, endogenous or exogenous. In a preferred embodiment, the polymerase (P) gene of the DNA virus hepatitis B virus is targeted for inhibition. Accordingly, in this embodiment, the target nucleic acid is at least the RNA transcript of the polymerase gene.

An effector sequence for a target is complementary to or substantially complementary to the predicted transcript of a region of the target gene. By "substantially complementary" it is meant that the sequences are hybridisable or annealable. Substantially complementary is preferably about 85% complementary to a portion of the target gene. More preferably, it is at least 85-90% complementary, and most preferably at least 95, 96, 97, 98 99 or 100% complementary. Substantial complementarity therefore includes 100% complementarity, but 100% complementarity may also be referred to throughout the specification as "complementary", or "being complementary".

A sequence complementary to or substantially complementary to a region of a target gene has the degree of sequence complementarity across a contiguous target sequence. Generally, a double stranded RNA region of the invention may be subjected to mutagenesis to produce single or several nucleotide substitutions, deletions or additions.

A "therapeutic composition" or "pharmaceutical composition" or "composition for treating HBV infection" refers to a composition including a ddRNAi agent, ddRNAi expression cassette, ddRNAi construct or siRNA agent.

The words "treat" or "treatment" refer to therapeutic treatment wherein the object is to slow down (lessen) an undesired physiological change or disorder. For purposes of this invention, beneficial or desired clinical results include, but are not limited to, alleviation of symptoms of HBV infection, reduced infectivity of HBV, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Treatment may not necessarily result in the complete clearance of HBV infection but may reduce or minimise complications and side effects of infection and the progression of infection.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) delays the onset of one or more symptoms of the particular disease, condition, or disorder described herein.

DETAILED DESCRIPTION

The current invention provides a new RNAi agent, and use of the RNAi agent for targeting HBV in infected individuals. Treatment of HBV is aimed at:
i. eliminating infectivity to prevent transmission and spread of HBV from one individual to another; and
ii. minimising the overall progression of liver disease within the infected individual. ddRNAi agent RNAi agents expressed from DNA based ddRNAi expression cassettes are referred to as DNA-directed RNAi agents, or ddRNAi agents. They can directly target the activity of genes with minimum off-target events. By "off target events" it is meant that expression of nucleic acids other than the target are not inhibited by the RNAi or ddRNAi agents. In the case of HBV infection, this offers a unique opportunity to address the unmet clinical treatment needs for HBV. Accordingly, in one aspect of the invention, there is provided a DNA-directed RNA interference (ddRNAi) agent for inhibiting expression of one or more target sequences in a Hepatitis B virus (HBV) gene, the ddRNAi agent comprising at least:
  a first effector sequence of at least 17 nucleotides in length; and
  a first effector complement sequence;
  wherein the first effector sequence is substantially complementary to the predicted transcript of a region of the target gene.

Typically, the first effector sequence forms a double stranded region with the first effector complement sequence.

The sequences of the ddRNAi agents of the invention have sufficient complementarity to a region of the HBV gene in order to mediate target specific RNAi. By "substantially complementary" it is meant that the sequences are hybridisable or annealable, and either:
  the sequence of the first effector sequence is at least about 80, 81, 82, 83, 84, 85, 86, 87, 88, 89 or 90% complementary to at least 17 or more contiguous nucleotides of the target sequence, more preferably at least about 90, 91, 92, 92, 94 or 95% complementary and even more preferably at least about 95, 96, 97, 98 or 99% complementary or absolutely complementary (ie 100%) to 17 or more contiguous nucleotides of the target sequence; or
  the effector sequence has at least 10 or more contiguous nucleotides that are 100% complementary with the target and preferably less than 6 nucleotides that cannot base pair with the target sequence. The first effector sequence can therefore have 1, 2, 3, 4 or 5 nucleotides that will not G-C/A-U base pair with the target sequence. It is believed that this level of difference will not negatively impact on the ability of the ddRNAi agent to be able to inhibit expression of the target sequence.

When the first effector sequence does have 1, 2, 3, 4 or 5 nucleotides that will not G-C/A-U base pair with the target sequence, it is preferred that the differences are in the first or last 5 nucleotides of the first effector sequence, with only 1 or 2 nucleotide changes in the centre portion of the effector sequence.

The ddRNAi agent may also comprise a first effector sequence consisting of 17, 18, 19, 20, 21, 22, 23, 24, 25, 26, 27, 28, 29, or 30 nucleotides in length, wherein the effector sequence is substantially complementary to the predicted transcript of a region of the target gene. A ddRNAi agent according to this embodiment of the invention therefore has a maximum length determined by the length and number of effector sequence/s ie each effector sequence is not comprised within a longer sequence.

As noted above, substantial complementarity is intended to mean that the sequences are hybridisable or annealable. The terms "hybridising" and "annealing" (and grammatical equivalents) are used interchangeably in this specification in respect of nucleotide sequences and refer to nucleotide sequences that are capable of forming Watson-Crick base pairs due to their complementarity. Preferably the substantially complementary sequences are able to hybridise under conditions of medium or high stringency:
  high stringency conditions: 0.1×SSPE (or 0.1×SSC), 0.1% SDS, 65° C.
  medium stringency conditions: 0.2×SSPE (or 1.0×SSC), 0.1% SDS, 50° C.

Alternatively, "substantially complementary" would also be understood by the person skilled in the art to involve non-Watson-Crick base-pairing, especially in the context of RNA sequences, such as a so-called "wobble pair" which can form between guanosine and uracil residues in RNA. "Complementary" is used herein in its usual way to indicate Watson-Crick base pairing, and "non-complementary" is used to mean non-Watson-Crick base pairing, even though such non-complementary sequences may form wobble pairs or other interactions. In the context of the present invention, reference to "non-pairing" sequences relates specifically to sequences between which Watson-Crick base pairs do not form.

The first effector sequence is at least 17 nucleotides long, preferably 17 to 50 nucleotides and most preferably 17 to 30 nucleotides. It may be 17, 18, 19, 20, 21, 22, 23, 24, 25, 26, 27, 28, 29 or 30 nucleotides in length. When the first effector sequence is longer than 17 nucleotides, it is preferred that at least 17 contiguous nucleotides of the first effector sequence forms the double stranded region with the complementary strand.

The ddRNAi agents of the invention inhibit expression of HBV nucleic acid sequences. Preferably, the HBV target gene is the nucleic acid sequence that is expressed as the polymerase (P) gene. Accordingly, in one embodiment of the invention, the ddRNAi agent of the invention inhibits expression of one or more target sequences in a Hepatitis B virus (HBV) polymerase gene. The HBV genome has overlapping open reading frames. As such, targeting particular sequences of the polymerase gene will also target the same sequences in the overlapping gene. The agents of the invention therefore are capable of targeting multiple genes with a single effector sequence. In each preferred embodiment however, at least the polymerase gene is targeted.

In particular embodiments, the first effector sequence is selected from any 10 or more and preferably any 17 or more contiguous nucleotides within any one of the ddRNAi HBV polymerase effector sequences SEQ ID NOS: 1-19, or SEQ ID NOS: 20-27 listed below. For simplicity, the SEQ ID NOS: will be collectively referred to as SEQ ID NOS: 1 to 27.

TABLE 1

RNAi effector sequences

| SEQ ID | RNAi effector sequence [a] | HBV Target Sites [b] | nts | Gene Target [c] |
|---|---|---|---|---|
| 1 | GAUUGACGAUAAGGGAGA | 109-126 | 18 | pol |
| 2 | UUGAAGUCCCAAUCUGGAU | 2935-2953 | 19 | pol |
| 3 | GCCGGGCAACGGGGUAAAGGUUC | 1139-1161 | 23 | pol |
| 4 | UAUUUGCGGGAGAGGACAACAGAGUUAUC | 1335-1363 | 29 | pol |
| 5 | UCCUGAUGUGAUGUUCUCCAUGU | 155-177 | 23 | pol & HBsAg |
| 6 | AAGGCCUCCGUGCGGUGGGG | 3019-3038 | 20 | pol |
| 7 | GGUAUUGUUUACACAGAAAGGC | 1116-1137 | 22 | pol |
| 8 | GAUGUGUUCUUGUGGCAAG | 908-926 | 19 | pol |
| 9 | GGGAAAGCCCUACGAACCACU | 698-718 | 21 | pol & HBsAg |
| 10 | GUGGAGACAGCGGGGUAGGC | 3128-3147 | 20 | pol |
| 11 | GAGGACAACAGAGUUAUC | 1335-1352 | 18 | pol |
| 12 | GCCCACUCCCAUAGGAAUUUUCC | 631-653 | 23 | pol & HBsAg |
| 13 | GGAUCUUGCAGAGUUUGG | 18-35 | 18 | pol |
| 14 | CGUUGCCGGGCAACGGGGUA | 1146-1165 | 20 | pol |
| 15 | GCAAUUUCCGUCCGAAGGUUUGG | 575-597 | 23 | pol & HBsAg |
| 16 | GUUGGAGGACAGGAGGUUGG | 340-359 | 20 | pol & HBsAg |
| 17 | GUUGGAGGACAGGAGGUUGGUG | 338-359 | 22 | pol & HBsAg |
| 18 | GAAGUGCACACGGUCCGGCAGA | 1568-1589 | 22 | pol & X |
| 19 | CAAGAUGCUGUACAGACUUGGC | 762-783 | 22 | pol & HBsAg |
| 20 | GGGAGAGGACAACAGAGUUAUC | 1335-1356 | 22 | pol |
| 21 | CGGGAGAGGACAACAGAGUUAU | 1336-1357 | 22 | pol |
| 22 | GCGGGAGAGGACAACAGAGUUA | 1337-1358 | 22 | pol |
| 23 | UGCGGGAGAGGACAACAGAGUU | 1338-1359 | 22 | pol |
| 24 | UUGCGGGAGAGGACAACAGAGU | 1339-1360 | 22 | pol |
| 25 | UUUGCGGGAGAGGACAACAGAG | 1340-1361 | 22 | pol |
| 26 | AUUUGCGGGAGAGGACAACAGA | 1341-1362 | 22 | pol |
| 27 | UAUUUGCGGGAGAGGACAACAG | 1342-1363 | 22 | pol |

[a] Sequence of effector sequence based on target of HBV genome according to Genbank ID U95551
[b] Target position within HBV genome, based on sequence of U95551; effector sequences are the reverse complement of these positions.
[c] ORFs targeted: pol corresponds to polymerase; HBsAg corresponds to the HBV surface antigen and X corresponds to the X protein As explained in the background section, both strands of a dsRNA have the potential to be the effector sequence. However there is evidence that particular features of a sequence can favour one strand to enter the RISC and the other strand to be destroyed. There is evidence that the protein Argonaut 2 (AGO2) of the RISC complex has a preference for sequences with a 5' A, and to a lesser extent a 5' U. In addition RNA sequences with a higher AU content in 5' regions seem to be preferentially loaded into RISC complexes, due to a mechanism that "senses" thermodynamic stability across RNA duplexes and favors incorporating sequences from the less stable end of the duplex. These sequence preferences are reflected in preferred embodiments, but are not essential.

For example, in one embodiment of this aspect of the invention, there is provided a DNA-directed RNA interference (ddRNAi) agent for inhibiting expression of one or more target sequences in a Hepatitis B virus (HBV) gene, the ddRNAi agent comprising at least:
  a first effector sequence of any 10 or more contiguous nucleotides within GAUUGACGAUAAGGGAGA (SEQ ID NO:1); and
  a first effector complement sequence.

The first effector sequence is substantially complementary to the predicted transcript of a region of the target gene.

Preferably the first effector sequence is at least 17 or more contiguous nucleotides within GAUUGAC-GAUAAGGGAGA (SEQ ID NO:1).

When the first effector sequence has 1, 2, 3, 4 or 5 nucleotides different to SEQ ID NO:1, the differences are preferably present in the first and/or last 5 nucleotides, and at least the centre 10 nucleotides are 100% complementary to the predicted transcript of a region of the target gene.

In alternative embodiments, the ddRNAi agent comprises a first effector sequence of any 10 or more, preferably any 17 or more, contiguous nucleotides within SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID: 19, SEQ ID NO: 20, SEQ ID NO: 21, SEQ ID NO: 22, SEQ ID NO: 23, SEQ ID NO: 24, SEQ ID NO: 25, SEQ ID NO: 26 and SEQ ID NO: 27.

In particularly preferred embodiments, the ddRNAi agent comprises a first effector sequence of any 10 or more, preferably any 17 or more, contiguous nucleotides within sequences able to inhibit the expression of a target gene region by at least 70%. Preferably, in this embodiment, the first effector is selected from SEQ ID NO:3, SEQ ID NO:9, SEQ ID NO:12, SEQ ID NO:13 and SEQ ID NO:23.

The first effector sequence may comprise a sequence selected from any 10 or more and preferably any 17 or more contiguous nucleotides within a sequence from the group consisting of SEQ ID NOS: 1-27, or alternatively, each effector sequence may be a variant of SEQ ID NOS:1-27, having 1, 2, 3, 4 or 5 nucleotide variations. In yet a further embodiment, each effector sequence may consist of 22 nucleotides, of which 17, 18, 19, 20, 21 or all 22 nucleotides are contiguous nucleotides from a sequence selected from the group consisting of SEQ ID NOS: 1-27.

Multiple Targeting ddRNAi Agents

In a preferred embodiment of the invention, the ddRNAi agent comprises two or more effector sequences to enable targeting of more than one target sequence of the HBV genome. The multiple target sequences may be in the same region of the HBV gene. For example, a 17 to 30 nucleotide region that has natural variation in the sequence between strains, or single nucleotide polymorphisms that have arisen to confer drug resistance. Alternatively, the target sequences may be in different regions of the one target gene.

To provide greater specificity the ddRNAi agent comprises the following (in no particular order):
  a first effector sequence of at least 17 nucleotides in length;
  a second effector sequence of at least 17 nucleotides in length;
  a first effector complement sequence; and
  a second effector complement sequence;

The first and second effector sequences of a multiple targeting ddRNAi agent form a double stranded region with their respective effector complements. Preferably, the first and second effector sequences are 17 to 30 nucleotides in length. More preferably, the first and second effector sequence are both selected from any 10 or more and preferably any 17 or more contiguous nucleotides within any one of the sequences listed in Table 1 above, or are sequences having 1, 2, 3, 4 or 5 nucleotides difference from those sequences listed in Table 1.

In one embodiment, the first effector sequence is selected from any 10 or more and preferably any 17 or more contiguous nucleotides within a sequence from any one of the group consisting of SEQ ID NOS:1-27, and the second effector sequence is selected from any 10 or more and preferably any 17 or more contiguous nucleotides within a sequence from any one of the group consisting of SEQ ID NOS: 1-27. The first and second effector sequence may both be the same sequence or may alternatively be different sequences.

The first and second effector sequence may each comprise a sequence selected from any 10 or more contiguous nucleotides within a sequence from the group consisting of SEQ ID NOS: 1-27, or alternatively, each effector sequence may also be a variant of SEQ ID NOS:1-27, having 1, 2, 3, 4 or 5 nucleotide variations. In yet a further embodiment, each effector sequence may consist of 22 nucleotides, of which 17, 18, 19, 20, 21 or all 22 nucleotides are contiguous nucleotides from a sequence selected from the group consisting of SEQ ID NOS: 1-27. When there are two or more effector sequences, they may represent a combination of the 3 types described above.

In particularly preferred embodiments, the first and second effector sequence comprise any 10 or more, preferably any 17 or more, contiguous nucleotides within sequences able to inhibit the expression of a target gene region by at least 70%. Preferably, in this embodiment, each effector sequence is selected from SEQ ID NO:3, SEQ ID NO:9, SEQ ID NO:12, SEQ ID NO:13 and SEQ ID NO:23.

The use of ddRNAi agents with multiple effector sequences has the advantage of limiting the emergence of and targeting escape mutants, which is a problem of many current anti-viral therapies. One aspect of the present invention neutralizes emergent escape mutants with a ddRNAi agent that contains RNAi sequences based upon the genetic sequence of the target gene and additionally sequences of the point mutations that arise to resist RNAi treatment.

Similarly, ddRNAi agents with multiple effector sequences have the advantage of being able to target a range of sequences found in different viral genotypes or quasi-species, as well as the advantage of the additive or synergistic effects achieved with multiple effector sequences as opposed to single effector sequences.

As mentioned above however, single effector sequences can achieve multiple targeting when the target sequence is common in 2 or more genes. HBV contains a number of overlapping reading frames, such that targeting a sequence in the overlapping regions will inhibit expression of both of the genes that contain that sequence.

Long Hairpin Version

Figure 1A:
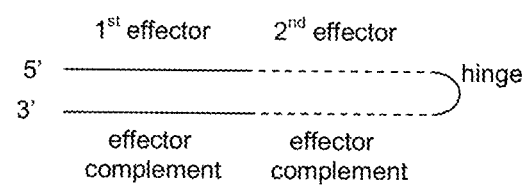

When the ddRNAi agent contains more than one effector sequence, and the ddRNAi agent is expressed as a single strand of RNA, it will fold to form different structures depending on the order of the effector sequences and the sequences complementary to the effector sequences. In one embodiment, there is provided a DNA-directed RNA interference (ddRNAi) agent for inhibiting expression of one or more target sequences in a Hepatitis B virus (HBV) gene, the ddRNAi agent comprising, in a 5' to 3' direction, at least:
  a first effector sequence of at least 17 nucleotides in length;
  a second effector sequence of at least 17 nucleotides in length;
  a second effector complement sequence; and
  a first effector complement sequence
wherein each effector sequence is substantially complementary to the predicted transcript of a region of the target gene. This will result in a ddRNAi agent with a structure as shown in FIG. 1A. See also WO2004/106517, incorporated herein by reference.

Alternatively, at least one effector, and preferably both effector sequences, are 100% complementary to the predicted transcript of a region of the target gene.

Preferably the first and second effector sequences are both selected from the group consisting of any 10 or more and preferably any 17 or more contiguous nucleotides within any one of SEQ ID NOS: 1-27. For example, in one embodiment, there is provided a DNA-directed RNA interference (ddRNAi) agent for inhibiting expression of one or more target sequences in a Hepatitis B virus (HBV) gene, the ddRNAi agent comprising, in a 5' to 3' direction, at least:
  a first effector sequence of any 10 or more contiguous nucleotides within GAUUGACGAUAAGGGAGA (SEQ ID NO:1);
  a second effector sequence of any 10 or more contiguous nucleotides within UUGAAGUCCCAAUCUGGAU (SEQ ID NO:2) or GCCGGGCAACGGGGUAAAGGUUC (SEQ ID NO:3);
  a second effector complement sequence; and
  a first effector complement sequence.

Each effector sequence is substantially complementary to the predicted transcript of a region of the target gene.

Alternatively, at least one effector, and preferably both effector sequences, are 100% complementary to the predicted transcript of a region of the target gene.

In particularly preferred embodiments, the first and second effector sequence comprise any 10 or more, preferably any 17 or more, contiguous nucleotides within sequences able to inhibit the expression of a target gene region by at least 70%. Preferably, in this embodiment, each effector sequence is selected from SEQ ID NO:3, SEQ ID NO:9, SEQ ID NO:12, SEQ ID NO:13 and SEQ ID NO:23.

In yet another embodiment, being an embodiment where the ddRNAi agent has 3 effector sequences, there is provided a DNA-directed RNA interference (ddRNAi) agent for inhibiting expression of one or more target sequences in a Hepatitis B virus (HBV) gene, the ddRNAi agent comprising, in a 5' to 3' direction, at least:
 a first effector sequence of any 10 or more contiguous nucleotides within GAUUGACGAUAAGGGAGA (SEQ ID NO:1);
 a second effector sequence of any 10 or more contiguous nucleotides within UUGAAGUCCCAAUCUGGAU (SEQ ID NO:2);
 a third effector sequence of any 10 or more contiguous nucleotides within GCCGGGCAACGGGGUAAAGGUUC (SEQ ID NO:3);
 a third effector complement sequence;
 a second effector complement sequence; and
 a first effector complement sequence.

Each effector sequence is substantially complementary to the predicted transcript of a region of the target gene.

Alternatively, at least one effector, and optionally 2 out of the 3 or all 3 of the effectors, are 100% complementary to the predicted transcript of a region of the target gene.

In particularly preferred embodiments, the first, second and third effector sequence comprise any 10 or more, preferably any 17 or more, contiguous nucleotides within sequences able to inhibit the expression of a target gene region by at least 70%. Preferably, in this embodiment, each effector sequence is selected from SEQ ID NO:3, SEQ ID NO:9, SEQ ID NO:12, SEQ ID NO:13 and SEQ ID NO:23.

It will also be appreciated by the skilled person that the order of effector and effector complements can be altered, provided that a single, long hairpin structure is formed by annealing of the effector sequence with its effector complement to form dsRNA. For example, in a 2-effector sequence ddRNAi agent, the sequences may be arranged in the following exemplary 5' to 3' orders:
 first effector-second effector-second effector complement-first effector complement;
 first effector-second effector complement-second effector-first effector complement;
 first effector complement-second effector complement-second effector-first effector;
 first effector complement-second effector-second effector complement-first effector.

In a 3-effector sequence ddRNAi agent, the sequences may be arranged in the following exemplary 5' to 3' orders:
 first effector-second effector-third effector-third effector complement-second effector complement-first effector complement
 first effector-second effector complement-third effector-third effector complement-second effector-first effector complement;
 first effector-second effector-third effector complement-third effector-second effector complement-first effector complement
 first effector complement-second effector complement-third effector complement-third effector-second effector-first effector complement
 first effector complement-second effector complement-third effector-third effector complement-second effector-first effector.

In yet further embodiments, the first effector sequence may be selected from any 10 or more and preferably any 17 or more contiguous nucleotides within a sequence from the group consisting of SEQ ID NOS:1-27; the second effector sequence may be selected from any 10 or more and preferably any 17 or more contiguous nucleotides within a sequence from the group consisting of SEQ ID NOS:1-27; the third effector sequence may be selected from any 10 or more and preferably any 17 or more contiguous nucleotides within a sequence from the group consisting of SEQ ID NOS:1-27; and any further effector sequences may be selected from any 10 or more and preferably any 17 or more contiguous nucleotides within a sequence from the group consisting of SEQ ID NOS:1-27. Alternatively, each effector sequence may also be a variant of SEQ ID NOS:1-27, having 1, 2, 3, 4 or 5 nucleotide variations. Preferably, the differences are present in the first and/or last 5 nucleotides, and at least the centre 11-12 nucleotides are 100% complementary to the predicted transcript of a region of the target gene. Such embodiments are particularly useful for targeting HBV escape mutants, as well as different viral genotypes or quasi-species.

The first, second and third effector sequence may each comprise a sequence selected from any 10 or more contiguous nucleotides within a sequence from the group consisting of SEQ ID NOS: 1-27, or alternatively, each effector sequence may also be a variant of SEQ ID NOS:1-27, having 1, 2, 3, 4 or 5 nucleotide variations. In yet a further embodiment, each effector sequence may consist of 22 nucleotides, of which 17, 18, 19, 20, 21 or all 22 nucleotides are contiguous nucleotides from a sequence selected from the group consisting of SEQ ID NOS: 1-27. When there are multiple effector sequences, they may represent a combination of the 3 types described above.

Multiple Hairpin Version

In an alternative embodiment, there is provided a DNA-directed RNA interference (ddRNAi) agent for inhibiting expression of one or more target sequences in a Hepatitis B virus (HBV) gene, the ddRNAi agent comprising, in a 5' to 3' direction, at least:
 a first effector sequence of at least 17 nucleotides in length;
 a first effector complement;
 a second effector sequence of at least 17 nucleotides in length; and
 a first effector complement wherein each effector sequence is substantially complementary to the predicted transcript of a region of the target gene.

Alternatively, at least one effector, and preferably both effector sequences, is 100% complementary to the predicted transcript of a region of the target gene.

Figure 1B:
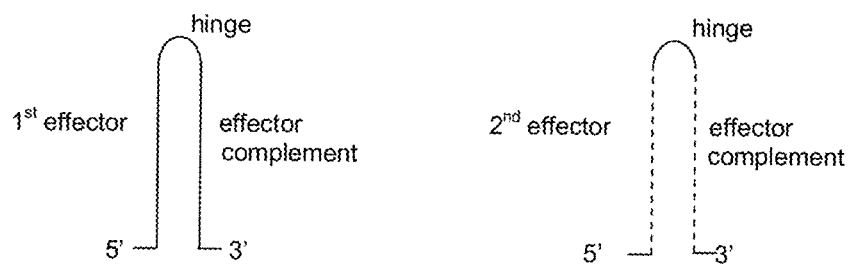
Figure 1C:
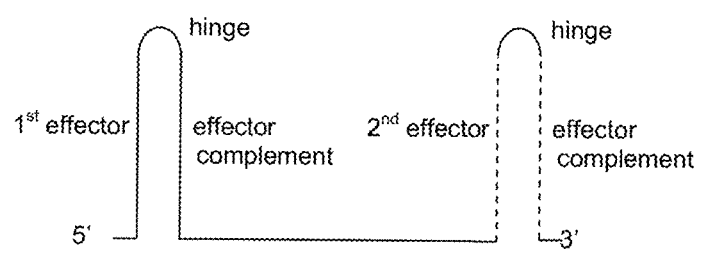

This will result in a ddRNAi agent with a structure as shown in FIG. 1B or C, depending on the type of expression cassette used to express it (see later in the specification). See also WO2005/087926 and WO2006/084209, incorporated herein by reference.

Preferably the first and second effector sequences are both selected from any 10 or more and preferably any 17 or more contiguous nucleotides within a sequence from the group consisting of SEQ ID NOS: 1-27. For example, in one embodiment, there is provided a DNA-directed RNA interference (ddRNAi) agent for inhibiting expression of one or more target sequences in a Hepatitis B virus (HBV) gene, the ddRNAi agent comprising, in a 5' to 3' direction, at least:
 a first effector sequence of any 10 or more contiguous nucleotides within GAUUGACGAUAAGGGAGA (SEQ ID NO:1);
 a first effector complement sequence;
 a second effector sequence any 10 or more contiguous nucleotides within UUGAAGUCCCAAUCUGGAU (SEQ ID NO:2) or GCCGGGCAACGGGGUAAAGGUUC (SEQ ID NO:3); and
 a second effector complement sequence.

Each effector sequence is substantially complementary to the predicted transcript of a region of the target gene.

Alternatively, at least one effector, and preferably both effector sequences, is 100% complementary to the predicted transcript of a region of the target gene.

In particularly preferred embodiments, the first and second effector sequence comprise any 10 or more, preferably any 17 or more, contiguous nucleotides within sequences able to inhibit the expression of a target gene region by at least 70%. Preferably, in this embodiment, each effector sequence is selected from SEQ ID NO:3, SEQ ID NO:9, SEQ ID NO:12, SEQ ID NO:13 and SEQ ID NO:23.

In an embodiment where the ddRNAi agent has 3 effector sequences, there is provided a DNA-directed RNA interference (ddRNAi) agent for inhibiting expression of one or more target sequences in a Hepatitis B virus (HBV) gene, the ddRNAi agent comprising, in a 5' to 3' direction, at least:
 a first effector sequence of any 10 or more contiguous nucleotides within GAUUGACGAUAAGGGAGA (SEQ ID NO:1);
 a first effector complement sequence;
 a second effector sequence of any 10 or more contiguous nucleotides within UUGAAGUCCCAAUCUGGAU (SEQ ID NO:2);
 a second effector complement sequence;
 a third effector sequence of any 10 or more contiguous nucleotides within GCCGGGCAACGGGGUAAAGGUUC (SEQ ID NO:3); and
 a third effector complement sequence.

Each effector sequence is substantially complementary to the predicted transcript of a region of the target gene.

Alternatively, at least one effector, and optionally 2 out of the 3 or all 3 of the effectors, is 100% complementary to the predicted transcript of a region of the target gene.

In particularly preferred embodiments, the first, second and third effector sequence comprise any 10 or more, preferably any 17 or more, contiguous nucleotides within sequences able to inhibit the expression of a target gene region by at least 70%. Preferably, in this embodiment, each effector sequence is selected from SEQ ID NO:3, SEQ ID NO:9, SEQ ID NO:12, SEQ ID NO:13 and SEQ ID NO:23.

In yet further embodiments, the first effector sequence may be any 10 or more contiguous nucleotides within a sequence selected from the group consisting of SEQ ID NOS:1-27; the second effector sequence may be any 10 or more contiguous nucleotides within a sequence selected from the group consisting of SEQ ID NOS:1-27; the third effector sequence may be any 10 or more contiguous nucleotides within a sequence selected from the group consisting of SEQ ID NOS:1-27; and any further effector sequences may be any 10 or more contiguous nucleotides within a sequence selected from the group consisting of SEQ ID NOS:1-27. Preferably, each effector sequence is at least 17 contiguous nucleotides.

Each effector sequence may also be a variant of SEQ ID NOS:1-27, having 1, 2, 3, 4 or 5 nucleotide variations. Preferably, the differences are present in the first and/or last 5 nucleotides, and at least the centre 10-12 nucleotides are 100% complementary to the predicted transcript of a region of the target gene. Such embodiments are particularly useful for targeting HBV escape mutants, as well as different viral genotypes or quasi species.

The first, second and third effector sequence may each comprise a sequence selected from any 10 or more contiguous nucleotides within a sequence from the group consisting of SEQ ID NOS: 1-27, or alternatively, each effector sequence may also be a variant of SEQ ID NOS:1-27, having 1, 2, 3, 4 or 5 nucleotide variations. In yet a further embodiment, each effector sequence may consist of 22 nucleotides, of which 17, 18, 19, 20, 21 or all 22 nucleotides are contiguous nucleotides from a sequence selected from the group consisting of SEQ ID NOS: 1-27. When there are multiple effector sequences, they may represent a combination of the 3 types described above. Furthermore, in the long hairpin structure or the multiple hairpin structure the ddRNAi agent may include additional effector sequences and corresponding complementary sequences according to one of the following formula:

Long Hairpin:
 [effector sequence]$_{1-10}$ [effector complement sequence]$_{1-10}$ Multiple Hairpin
 [effector sequence-effector complement sequence]$_{1-10}$ Preferably, in the long hairpin formula, the number of effector sequences is equal to the number of effector complement sequences. Typically, there are 2, 3, 4 or 5 effector sequences, and accordingly, 2, 3, 4 or 5 effector complement sequences respectively.

When the ddRNAi agent does contain more than one effector sequence, the effector sequences may be the same or different. For example, if a ddRNAi agent has 3 effector sequences, 2 effector sequences may have the same sequence, while 1 is different. Alternatively, all 3 effector sequences may be different. Preferably, the effector sequences are any 10 or more and preferably any 17 or more contiguous nucleotides within a sequence selected from the group consisting of SEQ ID NOS: 1-27, or variants of the sequences of SEQ ID NOS:1-27 which have 1, 2, 3, 4 or 5 nucleotide variations. Preferably, the differences are present in the first and/or last 5 nucleotides, and at least the centre 10-12 nucleotides are 100% complementary to the predicted transcript of a region of the target gene.

When targeting a single region of a target sequence that has naturally occurring variants (eg different genotypes or quasi-species), escape mutants, or single nucleotide polymorphisms (SNPs), it is preferable that at least one effector sequence is chosen from any 10 or more and preferably any 17 or more contiguous nucleotides within a sequence selected from the group consisting of SEQ ID NOS: 1-27, whereas other effector sequences are variants of that chosen sequence. For example, a first effector sequence may comprise 20 nucleotides of SEQ ID NO: 1; the second effector sequence should therefore be a variant of SEQ ID NO:1.

Hairpin Structures

In the above embodiments, the effector sequence hybridises with its corresponding effector complement sequence to form a hairpin structure. At the end of the hairpin, two or more unbound nucleotides form the 'hinge' or 'loop'. In one embodiment, the unbound nucleotides are part of the effector sequence and the effector complement sequence, such that only a portion of the at least 17 nucleotides of the effector sequence will form a duplex with its corresponding effector complement sequence. For example, when the effector sequence and its complement are both 22 nucleotides long, 19 of the nucleotides may base pair to form a double stranded region, leaving a total of 6 nucleotides (3 from each strand) to form a single stranded loop between and joining the effector sequence and its effector complement sequence.

In an alternative embodiment, an additional sequence that is non-complementary to itself, the target sequence, the effector sequence or the sequence complementary to the effector sequence may be included in the ddRNAi. As such, in yet another embodiment of the invention, the ddRNAi agent further includes a sequence of 2 to 100 unpaired nucleotides capable of forming a loop, more preferably, 2 to 10 unpaired nucleotides. In a preferred embodiment the loop includes the nucleotide sequence AA, UU, UUA, UUAG, UUACAA, CAAGAGA or N1AAN2, where N1 and N2 are any of C, G, U and A and may be the same or different.

Figure 1D:
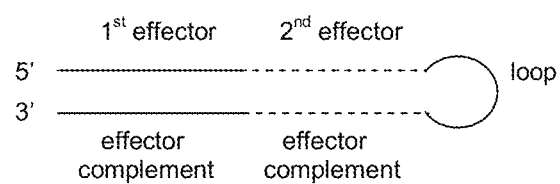

There may be one or more loops depending on the ddRNAi agent structure. When a ddRNAi agent has a long hairpin structure based on formula [effector sequence]1-10 [effector complement sequence]1-10 additional non-self-complementary sequence to give rise to a single loop structure is contained between the last effector sequence and the effector complement sequence of that last effector sequence, as illustrated in FIG. 1D. In this embodiment, there is therefore provided a DNA-directed RNA interference (ddRNAi) agent for inhibiting expression of one or more target sequences in a Hepatitis B virus (HBV) gene, the ddRNAi agent comprising, in a 5' to 3' direction, at least:
- a first effector sequence of at least 17 nucleotides in length;
- a second effector sequence of at least 17 nucleotides in length;
- a sequence of 2 to 100 non-self-complementary nucleotides;
- a second effector complement sequence; and
- a first effector complement sequence wherein each effector sequence is substantially complementary to the predicted transcript of a region of the target gene.

Figure 1E:
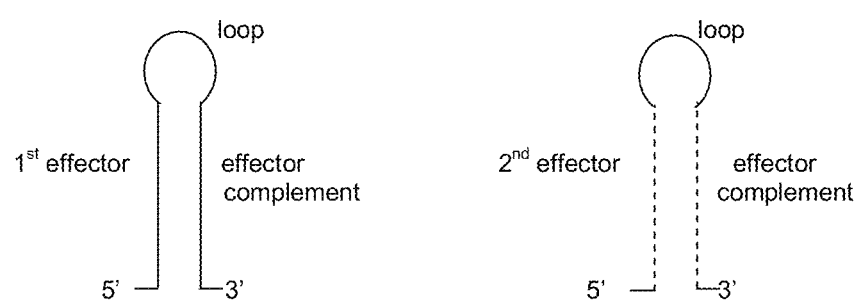
Figure 1F:
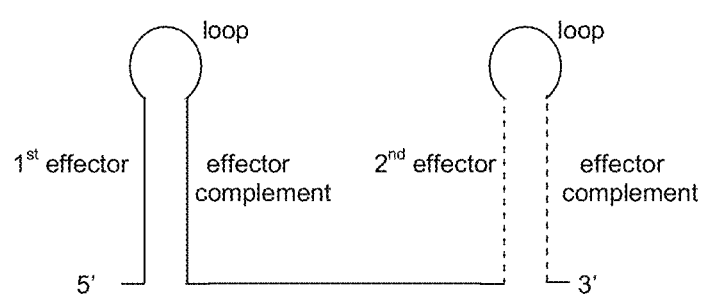

When the ddRNAi agent has a multiple hairpin structure based on formula [effector sequence-effector complement sequence]1-10 additional non-self-complementary sequence is contained between each effector sequence and its complementary sequence to give rise to a loop structure, as illustrated in FIGS. 1E and F (depending on the type of expression cassette used to express it (see later in the specification). In this embodiment, there is provided a DNA-directed RNA interference (ddRNAi) agent for inhibiting expression of one or more target sequences in a Hepatitis B virus (HBV) gene, the ddRNAi agent comprising, in a 5' to 3' direction, at least:
- a first effector sequence of at least 17 nucleotides in length;
- a sequence of 2 to 100 non-self-complementary nucleotides;
- a first effector complement sequence;
- a second effector sequence of at least 17 nucleotides in length;
- a sequence of 2 to 100 non-self-complementary nucleotides; and
- a second effector complement sequence wherein each effector sequence is substantially complementary to the predicted transcript of a region of the target gene.

In this embodiment where there are more than two effector and two effector complement sequences, and therefore more than two hairpin structures, the length of additional non-self-complementary sequence that forms each loop structure does not have to be the same. For example, one loop structure may have 5 nucleotides, while another loop structure may have 9 nucleotides.

2 Strand ddRNAi Agents

As will be appreciated by one skilled in the art, it is not necessary that the entire ddRNAi agent is expressed as one sequence. For example, in one embodiment of the invention, the first effector sequence may be generated (e.g., transcribed by one DNA sequence), and the first effector complement sequence may be generated (e.g., transcribed from a separate DNA sequence). Optionally, a loop sequence may be attached to either transcript or part of the loop attached to the 3' end of one transcript and the 5' end of the other transcript. Within the cell, the two transcripts then form the ddRNAi agent by hybridising through annealing between the effector sequence/s and their complement/s.

In Vitro Expressed ddRNAi Agents or Chemically Synthesised siRNA Agents

While it is envisaged that effective treatment of chronic HBV infection will require ddRNAi agents to be expressed in vivo from ddRNAi constructs (as will be outlined below), there may be circumstances where it is desirable to administer ddRNAi agents that are expressed in vitro or to administer siRNAs that are chemically synthesised, thereby functioning as more of a transient therapy. Acute HBV infection for example may benefit from a short term treatment with siRNAs that do not integrate and replicate in the cells.

The ddRNAi agents of the invention may therefore be expressed in vitro and then delivered to target cells. Alternatively, siRNAs may be chemically synthesised and then delivered to the target cells. In light of this, in another aspect of the invention, there is provided a small interfering RNAi agent (siRNA agent) for inhibiting expression of one or more target sequences in a Hepatitis B virus (HBV) gene, the siRNA comprising
- a first effector sequence of at least 17 nucleotides in length; and
- a first effector complement sequence;

wherein the effector sequence is substantially complementary to the predicted transcript of a region of the target gene.

Similarly to the ddRNAi agents described above, the siRNA agent may also include more than one effector sequence for multiple targeting. The effector sequences preferably target the HBV polymerase gene, and most preferably, are selected from any 10 or more and preferably any 17 or more contiguous nucleotides within a sequence from the group consisting of SEQ ID NOS: 1-27.

Considerable flexibility is possible in the design of siRNAs. Typically siRNAs consist of dsRNA molecules with 5'-phosphate and 3'-hydroxyl residues, strand lengths can vary from 21-29 nucleotides and may optionally be designed to include 2 nucleotide 3' overhangs. In some embodiments each strand can be synthesised as N19-27TT (where TT can be deoxyribonucleotides). siRNAs can be readily designed based on regions of SEQ ID NOS: 1-27 as described above and can be used therapeutically as single sequences or in any combinations. Alternatively siRNA agents can consist of single RNA molecules containing effector and effector complement sequences similar or identical to those expressed from ddRNAi expression cassettes. These sequences can be based on SEQ ID NOS: 1-27 and can be used therapeutically as single sequences or in any combination. The siRNAs can be chemically synthesized with appropriately protected ribonucleoside phosphoramidites and a conventional synthesizer and thus are widely available commercially and able to be designed and synthesised according to routine methods in the art. In preferred embodiments, the siRNAs have the sequences of any 10 or more contiguous nucleotides within a sequence from one or more of SEQ ID NOS:1-27.

A number of transfection reagents have been used for delivering siRNA into different cell lines. Lipofectamine 2000 and Oligofectamine are routinely used for siRNA delivery. Naked siRNAs have also been delivered by hydrodynamic transfection methods. Other delivery methods would be known by the skilled person.

ddRNAi Agent Expression Cassettes

As explained above, ddRNAi agents are expressed from DNA expression cassettes inserted into any suitable vector or ddRNAi construct. ddRNAi expression cassettes comprise (in no particular order):
one or more promoter sequences
one or more DNA sequences that encode for one or more effector sequences
one or more DNA sequences that encode for one or more effector complement sequences;
one or more terminator sequences
and optionally
one or more DNA sequences that encode for loop sequences
one or more enhancer sequences.

In one embodiment, there is provided a DNA-directed RNA interference (ddRNAi) expression cassette for expressing a ddRNAi agent, wherein the ddRNAi agent inhibits expression of one or more target sequences in a Hepatitis B virus (HBV) gene, the ddRNAi expression cassette comprising, in a 5' to 3' direction:
a promoter sequence
a DNA sequence that encodes for a first effector sequence
optionally a sequence that encodes for sequence capable of forming a loop
a DNA sequence that encodes for a first effector complement sequence; and
a terminator sequence.

The DNA sequence that encodes for the first effector sequence is preferably a DNA that encodes for 10 or more, preferably 17 or more, contiguous nucleotides within a sequence from any one of SEQ ID NOS: 1-27. In particularly a preferred embodiment, the first effector sequence comprise any 10 or more, preferably any 17 or more, contiguous nucleotides within sequences able to inhibit the expression of a target gene region by at least 70%. Preferably, in this embodiment, the first effector sequence is selected from SEQ ID NO:3, SEQ ID NO:9, SEQ ID NO:12, SEQ ID NO:13 and SEQ ID NO:23.

Alternatively, as outlined above in relation to the ddRNAi agent itself, the sequence that encodes for the effector sequence may encode an effector sequence that varies by 1, 2, 3, 4 or 5 nucleotides from SEQ ID NOS:1-27 without affecting the ability of the effector sequence encoded to base pair with the target sequence and inhibit expression of the target sequence.

The skilled person would appreciate that a DNA sequence encoding any given RNA sequence is the same sequence as the RNA but having thymine (T) bases instead of uracil (U) bases.

The ddRNAi expression cassettes encoding ddRNAi agents having more than one effector sequence in a long hairpin structure comprise, in a 5' to 3' direction:
a promoter sequence;
a DNA sequence that encodes for a first effector sequence;
a DNA sequence that encodes for a second effector sequence;
optionally a sequence that encodes for sequence capable of forming a loop;
a DNA sequence that encodes for a second effector complement sequence;
a DNA sequence that encodes for a first effector complement sequence; and
a terminator sequence.

Preferably the DNA sequences encode first and second effector sequence selected from any 10 or more and preferably any 17 or more contiguous nucleotides within a sequence from the group consisting of SEQ ID NOS: 1-27. Preferably, the first and second effector sequence is selected from SEQ ID NO:3, SEQ ID NO:9, SEQ ID NO:12, SEQ ID NO:13 and SEQ ID NO:23. Alternatively, the DNA sequences encode for an effector sequence that varies from SEQ ID NOS: 1-27 by 1, 2, 3, 4 or 5 nucleotides without affecting the ability of the effector sequence encoded to base pair with the target sequence and inhibit expression of the target sequence.

When the ddRNAi agent has more than one effector sequence and a multiple hairpin structure based on formula [effector sequence-effector complement sequence]1-10 expression of each [effector sequence-effector complement sequence] pair may be controlled by a single promoter, or alternatively by a separate promoter. When separate promoters are contemplated, the ddRNAi expression cassette comprises, in a 5' to 3' direction:
a promoter sequence
a DNA sequence that encodes for a first effector sequence
a DNA sequence that encodes for a first effector complement sequence;
optionally a terminator sequence;
a promoter sequence;
a DNA sequence that encodes for a second effector sequence;
a DNA sequence that encodes for a second effector complement sequence; and
a terminator sequence.

When a single promoter is contemplated, the ddRNAi expression cassette comprises, in a 5' to 3' direction:
a promoter sequence
a DNA sequence that encodes for a first effector sequence
a DNA sequence that encodes for an effector complement sequence to the first effector sequence;
a DNA sequence that encodes for a second effector sequence;
a DNA sequence that encodes for an effector complement sequence to the second effector sequence; and
a terminator sequence.

Similarly to the above embodiments, the DNA sequences preferably encode first and second effector sequence selected from any 10 or more and preferably any 17 or more contiguous nucleotides within a sequence from the group consisting of SEQ ID NOS:1-27, or. effector sequences that vary in sequence from SEQ ID NOS: 1-27 by 1, 2, 3, 4 or 5 nucleotides. Preferably, the first and second effector sequence is selected from SEQ ID NO:3, SEQ ID NO:9, SEQ ID NO:12, SEQ ID NO:13 and SEQ ID NO:23.

The ddRNAi expression cassette may alternatively be described by reference to the total length of the ddRNAi agent expressed, which is a product of the total length of sequence between the promoter and terminator. For example, when the length of the effector sequence in a single effector ddRNAi consists of 17, 18, 19, 20, 21, 22, 23, 24, 25, 26, 27, 28, 29, or 30 nucleotides, the ddRNAi expression cassette will have a length of 34 to 60 nucleotides between the promoter and terminator. This length may further include 2 to 100 nucleotides of "loop" or "hinge" sequence, giving a length of between 36 to 160 nucleotides. For ddRNAi agents having multiple effector sequences, where each effector sequence consists of 17, 18, 19, 20, 21, 22, 23, 24, 25, 26, 27, 28, 29, or 30 nucleotides, the overall length is increased proportionally.

One useful way of designing ddRNAi expression cassettes of the invention is to assume Dicer cuts every 22 nucleotides (also referred to as 22 nt phasing), and processes from the base of the shRNA. The DNA sequences that encode effector sequences can therefore be designed to encode any 10 or more, and preferably any 17 or more contiguous nucleotides within a sequence from the group consisting of SEQ ID NOS:1-27, together with appropriate spacers and other sequence requirements for the appropriate promoter. For example, some of the sequences listed in SEQ ID NOS: 1-27 are greater than 22 nucleotides; in these instances only a portion of the sequence needs to be operably linked to a promoter.

Agents targeting different sites of mRNA are suitable for shRNA construction, because they can avoid the influence of secondary structures of mRNA, and thus perform their functions independently.

When a U6 promoter is used, it is preferable that the DNA sequence operably linked to the promoter starts with a guanine (G) base; when a H1 promoter is used, it is preferable that the DNA sequence operably linked to the promoter starts with an adenine (A) base. The effector encoding sequence can therefore be modified accordingly. For some sequences from SEQ ID NOS: 1-27, effector sequences are shorter than 22 nts; in these instances it is preferable to include HBV sequences adjacent to the HBV target sites. This would serve to maximise homology of effector sequences to HBV mRNAs and might also permit the inclusion of A or G residues to allow efficient transcriptional initiation from the U6 or H1 promoters as described above. Moreover, for US transcription in particular, the effector sequence is desirably placed 3' of the loop to avoid the 5' G necessary for efficient U6 transcription.

In some instances it may be desirable to avoid the DNA sequence TTTT within effector, effector complement or loop sequences since these can act as transcriptional terminators in expression constructs which use Pol III promoters such as U6 or H1. shRNA design should also take in to account that U6 termination is expected to add a UU to the 3' end to the shRNA. When designing long hairpin RNAs, it is sometimes advantageous to modify the precise choice of effector sequences (either using sequences from, or adjacent to SEQ ID NOS: 1-27) to maximise the likelihood that Dicer processed effector sequences will include a 5'U or A, thereby encouraging incorporation into AGO2.

The choice of whether to control expression of each [effector sequence-effector complement sequence] pair depends on a number of factors. A single promoter may be utilised to minimise interference between promoters. A ddRNAi construct with only a single promoter is also smaller in size, which can be important in some cases for the stability of the construct, both during production (eg replication in E. coli) and delivery. In addition, the use of a single promoter avoids the possibility of any homologous recombination between promoters.

In circumstances where a degree of regulation of expression of each effector sequence or complement is required though, it is advantageous to design a ddRNAi construct having multiple promoters, whereby expression of each [effector sequence-effector complement sequence] pair is controlled by a separate promoter. In circumstances where the effector sequences are of a different sequence, the nature of the sequence may mean one sequence is expressed to higher expression levels. When it is desired to ensure more equal expression levels of each effector sequence, the more highly expressed effector sequence can be paired with a weaker promoter and vice versa. Moreover, more efficient expression may be achieved as the length of any one sequence to be transcribed is shorter. When multiple promoters are used, it is preferable that not all of the promoters are the same to minimise the risk of any homologous recombination between them. In the case of 2 promoters, each is preferably different. In the case of 3 promoters, at least 2 and optionally all 3 are different from one another.

The DNA sequence encoding the effector sequence is operably linked to the promoter sequence. A sequence is "operably linked" to another nucleotide sequence when it is placed in a functional relationship with another nucleotide sequence. For example, if a coding sequence is operably linked to a promoter sequence, this generally means that the promoter promotes transcription of the coding sequence. Operably linked means that the DNA sequences being linked are typically contiguous and, where necessary to join two protein coding regions, contiguous and in reading frame. However, since enhancers may function when separated from the promoter by several kilobases and intronic sequences may be of variable length, some nucleotide sequences may be operably linked but not contiguous.

A "promoter" or "promoter sequence" or "promoter element" is generally a DNA regulatory region capable of binding RNA polymerase in a cell and initiating transcription of a polynucleotide or polypeptide coding sequence such as mRNA or any kind of RNA transcribed by any class of any RNA polymerase. The promoter and terminator may be taken from different genes, but are typically matched to each other; that is, the promoter and terminator sequences or elements are taken from the same gene in which they occur naturally. Promoters also may or may not be modified using molecular techniques, or otherwise, e.g., through mutation of regulatory elements such as enhancers, to attain higher or lower levels of transcription.

The term "constitutive" when made in reference to a promoter means that the promoter is capable of directing transcription of an operably linked nucleic acid sequence in the presence or absence of a specific stimulus (e.g., heat shock, chemicals, light, etc.). Typically, constitutive promoters are capable of directing expression of a coding sequence in substantially any cell and any tissue. The promoters used in the expression cassettes to transcribe the ddRNAi agents preferably are constitutive promoters, such as the promoters for ubiquitin, CMV, β-actin, histone H4, EF-1alfa or pgk genes whose expression is controlled by RNA polymerase II binding to the promoter, or promoter elements which are bound by RNA polymerase I. In other embodiments, a Pol Il promoter such as CMV, SV40, hAAT, U1, β-actin or a hybrid Pol Il promoter is employed. In other embodiments, promoter elements bound by RNA polymerase III are used, such as the U6 promoters (U6-1, U6-8, U6-9, e.g.), H1 promoter, 7SL promoter, the human Y promoters (hY1, hY3, hY4 (see Maraia, et al., Nucleic Acids Res 22 (15):3045-52 (1994)) and hY5 (see Maraia, et al., Nucleic Acids Res 24 (18):3552-59 (1994)), the human MRP-7-2 promoter, Adenovirus VA1 promoter, human tRNA promoters, the 5S ribosomal RNA promoters, as well as functional hybrids and combinations of any of these promoters. Variants of these promoters may also be utilised, wherein the promoter is modified to decrease or increase its activity. For example, if a strong promoter causes too much expression of the sequence operably linked to it, it can be modified to decrease its activity.

When a U6 promoter is used, it is preferable that the DNA sequence operably linked to the promoter starts with a guanine (G) base; when a H1 promoter is used, it is preferable that the DNA sequence operably linked to the promoter starts with an adenine (A) base. The sequences of the nucleic acids may therefore favour the use of one promoter over another.

Alternatively in some embodiments it may be optimal to select promoters that allow for inducible expression of the multiple ddRNAi agents expressed from the ddRNAi construct. A number of systems for inducible expression using such promoters are known in the art, including but not limited to the tetracycline responsive system and the lac operator-repressor system (see WO 03/022052 A1 Publication; and U.S. Patent Publication 2002/0162126 A1), the ecdysone regulated system, or promoters regulated by glucocorticoids, progestins, estrogen, RU-486, steroids, thyroid hormones, cyclic AMP, cytokines, the calciferol family of regulators, or the metallothionein promoter (regulated by inorganic metals).

Promoters useful in some embodiments of the present invention may be tissue-specific or cell-specific. The term "tissue-specific" as it applies to a promoter refers to a promoter that is capable of directing selective expression of a nucleotide sequence of interest to a specific type of tissue in the relative absence of expression of the same nucleotide sequence of interest in a different type of tissue (e.g., brain). The term "cell-specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell-specific" when applied to a promoter also means a promoter capable of promoting selective expression of a nucleotide sequence of interest in a region within a single tissue. Alternatively, promoters may be constitutive or regulatable. Additionally, promoters may be modified so as to possess different specificities.

In the case of HBV infection, liver specific promoters may be utilised. Examples of liver specific promoters are human Alpha Antitrypsin promoter (hAAT) apolipoprotein H (ApoH) and Lecithin Cholesterol Acetyl Transferase promoter (LCAT). Alternatively, the transthyretin or TTR promoter may be utilised. The TTR promoter is derived from the mouse prealbumin gene and is also referred to as prealbumin. The full length TTR promoter normally controls expression of the serum thyroxine-binding protein, which is made by hepatocytes and by the choroid plexus epithelium in adults. In one embodiment, a preferred TTR promoter is a TTR promoter in which the region which controls choroids plexus expression is deleted, but retains the regions which drive liver-specific expression. See for example WO2007/120533 and US20060189561, incorporated herein by reference.

As noted above, enhancer elements are optionally included in the ddRNAi constructs of the invention. One preferred enhancer element is ApoE. The ApoE enhancer element consists of approximately 155 bp derived from apolipoprotein E (ApoE). ApoE mediates binding, internalization and catabolism of lipoprotein particles and is a ligand for the low-density lipoprotein (ApoB/E) receptor and for the ApoE receptor of hepatic tissues. The genetic enhancer associated with the ApoE gene is a eukaryotic control element that can increase transcription of a nucleic acid specifically in the liver. The ApoE enhancer may be located up to 2000 nucleotides upstream or downstream of a liver specific promoter, and may be present in more than one copy. An ApoE/hAAT is one preferred enhancer/promoter combination.

Alternatively, a synthetic enhancer (SynEnh) may be used, such as that described in US20060189561 (incorporated herein by reference).

When the ddRNAi expression cassette or construct contains more than one terminator sequence or element, the terminator sequences or elements may be the same, or different, or there may be a combination of termination elements represented only once and termination elements represented two times or more within any cassette. Whatever terminator sequences or elements are used they should be selected to ensure that they work appropriately with the liver-specific promoter used. In instances where Pol I, Pol III or Pol III promoters are used, appropriate terminator sequences should be employed. Termination elements useful in the present invention include the U1 termination sequence (U1 box), the synthetic polyA terminator, and the so called minimal PolyA terminator. Transcriptional pause sites, such as MAZ1 and MAZ2, (See Ashfield et al EMBO J 1994 Vol 13 No 23 5656 pp and Yonaha and Proudfoot EMBO J. 2000 Jul. 17; 19 (14):3770-7) may be inserted upstream of the polyA terminators to assist in coupling of transcription termination and polyadenylation. For Pol III promoters, the sequences TTTT, TTTTT or TTTTTT are commonly used as terminators. In these instances transcripts are typically terminated by the sequence UU.

Delivery of the ddRNAi Constructs—Viral Based ddRNAi Constructs

A challenge in developing any HBV therapeutic is that virtually all hepatocytes in the patients are infected. As such, a means of achieving efficient and uniform transduction of all liver cells with the ddRNAi agent of the invention is required to provide an effective gene therapy for chronic HBV infection. Moreover, for effective in vivo treatment of HBV infection, the ddRNAi expression cassette of the invention has to be able to be transfected into primary cells, stem cells, and non-dividing cells.

To overcome this limitation, the ddRNAi expression cassettes of the invention are introduced into a delivery vector, preferably derived from viruses to ensure compatibility with viral delivery, to generate ddRNAi constructs. As noted earlier, the vector backbone may serve the dual purpose of being an expression vector as well as a delivery vector. Generation of the construct can be accomplished using any suitable genetic engineering techniques well known in the art, including without limitation, the standard techniques of PCR, oligonucleotide synthesis, DNA synthesis, restriction endonuclease digestion, ligation, transformation, plasmid purification, and DNA sequencing. The construct preferably comprises, for example, sequences necessary to package the ddRNAi construct into viral particles and/or sequences that allow integration of the ddRNAi construct into the target cell genome. The viral construct also may contain genes that allow for replication and propagation of virus, though in preferred embodiments such genes will be supplied in trans. Additionally, the ddRNAi construct may contain genes or genetic sequences from the genome of any known organism incorporated in native form or modified. For example, the preferred viral construct comprises sequences useful for replication of the construct in bacteria.

The viral vector backbone may be selected from lentiviral, adenoviral (Adv), and adeno-associated viral (AAV) vectors. Non-integrating viral vectors may be used for transient expression in dividing cells of ddRNAi agents of the invention or for longer term stable expression in non-dividing cells. Integrating viral vectors, such as lentiviral vectors, mediate stable, long term expression in both dividing and non-dividing cells.

Alternatively, minicircles such as those described in US20040214329 may be used to deliver the ddRNAi expression cassettes. Minicircles provide for persistently high levels of nucleic acid transcription, and are characterised by being devoid of expression-silencing bacterial sequences.

AAV vectors are non-pathogenic and less immunogenic compared with other viral vectors. The ability of AAV vectors to infect both dividing and non-dividing cells, and to direct long-term gene expression in these tissues makes it a useful vehicle for gene therapy. Moreover, AAV has a variety of pseudotypes with different tissue tropisms. A preferred AAV vector is the double stranded AAV pseudotype 8 (dsAAV8).

Typically, the genome of AAV contains only two genes. The "rep" gene codes for at least four separate proteins utilized in DNA replication. The "cap" gene product is spliced differentially to generate the three proteins that comprise the capsid of the virus. When packaging the genome into nascent virus, only the Inverted Terminal Repeats (ITRs) are obligate sequences; rep and cap can be deleted from the genome and be replaced with heterologous sequences of choice. However, in order to produce the proteins needed to replicate and package the AAV-based heterologous construct into nascent virion, the rep and cap proteins must be provided in trans. The helper functions normally provided by co-infection with the helper virus, such as adenovirus or herpesvirus, can also be provided in trans in the form of one or more DNA expression plasmids. Since the genome normally encodes only two genes it is not surprising that, as a delivery vehicle, AAV is limited by a packaging capacity of 4.5 single stranded kilobases (kb). However, although this size restriction may limit the genes that can be delivered for replacement gene therapies, it does not adversely affect the packaging and expression of shorter sequences such as ddRNAi vectors.

Accordingly, in another aspect of the invention, there is provided a ddRNAi construct comprising a viral vector into which a ddRNAi expression cassette according to the invention is inserted. Preferably the expression cassette encodes for multiple RNAi agents, as either long hairpin structures or multiple hairpin structures. In one embodiment, the viral vector is an AAV vector.

After generation of the viral based ddRNAi construct, the construct is packaged into viral particles. Any method known in the art may be used to produce infectious viral particles whose genome comprises a copy of the viral ddRNAi construct. One method utilizes packaging cells that stably express in trans the viral proteins that are required for the incorporation of the viral ddRNAi construct into viral particles, as well as other sequences necessary or preferred for a particular viral delivery system (for example, sequences needed for replication, structural proteins and viral assembly) and either viral-derived or artificial ligands for tissue entry. Following transfection of the viral ddRNAi construct into packaging cells, the packaging cells then replicate viral sequences, express viral proteins and package the ddRNAi expression constructs into infectious viral particles. The packaging cell line may be any cell line that is capable of expressing viral proteins, including but not limited to 293, HeLa, A549, PerC6, D17, MDCK, BHK, bing cherry, phoenix, Cf2Th, or any other line known to or developed by those skilled in the art. One packaging cell line is described, for example, in U.S. Pat. No. 6,218,181.

Alternatively, a cell line that does not stably express necessary viral proteins may be co-transfected with one or more constructs to achieve efficient production of functional particles. One of the constructs is the viral based ddRNAi construct; the other construct comprises nucleic acids encoding the proteins necessary to allow the cells to produce functional virus as well as other helper functions.

The packaging cell line or replication and packaging construct may not express envelope gene products. In these embodiments, the gene encoding the envelope gene can be provided on a separate construct that is co-transfected with the viral based ddRNAi construct. As the envelope protein is responsible, in part, for the host range of the viral particles, the viruses may be pseudotyped. As described supra, a "pseudotyped" virus is a viral particle having an envelope protein that is from a virus other than the virus from which the genome is derived. One with skill in the art can choose an appropriate pseudotype for the viral delivery system used and cell to be targeted. In addition to conferring a specific host range, a chosen pseudotype may permit the virus to be concentrated to a very high titer. Viruses alternatively can be pseudotyped with ecotropic envelope proteins that limit infection to a specific species (e.g., ecotropic envelopes allow infection of, e.g., murine cells only, where amphotropic envelopes allow infection of, e.g., both human and murine cells). In addition, genetically-modified ligands can be used for cell-specific targeting, such as the asialoglycoprotein for hepatocytes, or transferrin for receptor-mediated binding.

After production in a packaging cell line, the viral particles containing the ddRNAi expression cassettes are purified and quantified (titred). Purification strategies include density gradient centrifugation, or, preferably, column chromatographic methods.

Methods of Treatment

Administration of ddRNAi agents, ddRNAi constructs or siRNA agents of the invention inhibit expression of HBV genes expressed in a cell infected with HBV. Accordingly, in another aspect of the invention, there is provided a method of treating HBV infection in a subject comprising providing a therapeutically effective amount of a ddRNAi agent to a patient in need of treatment, wherein the ddRNAi agent inhibits expression of one or more target sequences in a Hepatitis B virus (HBV) gene, preferably the polymerase gene of HBV. The ddRNAi agent to be administered to the patient may be one or more of:

a ddRNAi agent comprising a first effector sequence; and a first effector complement sequence; wherein the effector sequence is substantially complementary to the predicted transcript of a region of the target gene ddRNAi agent comprising, in a 5' to 3' direction, a first effector sequence; a second effector sequence; a second effector complement sequence; and a first effector complement sequence, wherein each effector sequence is substantially complementary to the predicted transcript of a region of the target gene a ddRNAi agent comprising, in a 5' to 3' direction, a first effector sequence; a second effector sequence; a third effector sequence; a third effector complement sequence; a second effector complement sequence; and a first effector complement sequence wherein each effector sequence is substantially complementary to the predicted transcript of a region of the target gene a ddRNAi agent comprising, in a 5' to 3' direction, a first effector sequence; a first effector complement sequence; a second effector sequence; and a second effector complement sequence wherein each effector sequence is substantially complementary to the predicted transcript of a region of the target gene a ddRNAi agent comprising, in a 5' to 3' direction, a first effector sequence; a first effector complement sequence; a second effector sequence; a second effector complement sequence; a third effector sequence; and a third effector complement sequence; wherein each effector sequence is substantially complementary to the predicted transcript of a region of the target gene a ddRNAi agent comprising, in a 5' to 3' direction, a first effector sequence; a second effector sequence; a sequence of 2 to 100 non-self-complementary nucleotides; a second effector complement sequence; and a first effector complement sequence wherein each effector sequence is substantially complementary to the predicted transcript of a region of the target gene a ddRNAi agent comprising, in a 5' to 3' direction, a first effector sequence; a sequence of 2 to 100 non-self-complementary nucleotides; a first effector complement sequence; a second effector sequence; a sequence of 2 to 100 non-self-complementary nucleotides; and a second effector complement sequence wherein each effector sequence is substantially complementary to the predicted transcript of a region of the target gene.

As would be understood by one skilled in the art, and as illustrated in the Figures, any particular effector sequence may be swapped in position with its complement in the agent. In particular forms of each of the embodiments described above, each effector sequence is at least 17 nucleotides in length selected from the group consisting of any 10 or more and preferably any 17 or more contiguous nucleotides within a sequence from any one of SEQ ID NOS: 1-27. The effector sequences may all be the same, or may all be different, or may be a combination eg 2 effector sequences of at least 10 contiguous nucleotides of SEQ ID NO:1 and 1 effector sequence of at least 10 contiguous nucleotides of SEQ ID NO: 4.

Preferably, the effector sequence is selected from the group consisting of any contiguous 11, 12, 13, 14, 15 or 16 nucleotides within any one of SEQ ID NOS: 1-27, and most preferably 17 or more contiguous nucleotides within any one of SEQ ID NOS: 1-27. Typically, the effector complement will be the same length, or about the same length (ie ±15% nucleotide length) as its corresponding effector sequence.

Each of these ddRNAi agents may be administered via a ddRNAi expression cassette in a ddRNAi construct, as described in the earlier sections of the specification. Multiple targeting may be achieved by delivering two or more ddRNAi expression cassettes or constructs each capable of expressing a single ddRNAi agent, or alternatively, by delivering one or more ddRNAi expression cassettes or constructs each capable of expressing more than one ddRNAi agent.

In alternative embodiments, each of the effector sequences may be 100% complementary to the predicted transcript of a region of the target gene, or may only vary by 1, 2, 3, 4 or 5 nucleotides.

The method of treating HBV infection can optionally include a preliminary step of identifying an individual having HBV infection including identification of the serotype of the HBV isolate.

For longer term or stable provision of the ddRNAi agents of the invention, the ddRNAi agent is provided via a ddRNAi construct of the invention ie in vivo expression of the ddRNAi agent from a ddRNAi expression cassette inserted into a suitable vector delivered to the cell. The ddRNAi expression cassette comprises:

one or more promoter sequences one or more DNA sequences selected from the group consisting of sequences that encode for any 10 or more contiguous nucleotides within a sequence from SEQ ID NOS: 1-27;

one or more DNA sequences that encode for one or more effector complement sequences;

one or more terminator sequences and optionally one or more DNA sequences that encode for loop sequences one or more enhancer sequences.

As outlined earlier in the specification, these components of the ddRNAi expression cassette may have different 5' to 3' arrangements, all of which are suitable for use in the methods of the invention.

In the methods of the invention, the HBV target gene is at least the polymerase (P) gene, and potentially the surface antigen or X gene when the target sequence is contained within overlapping open reading frames, and the ddRNAi agent comprises ddRNAi effector sequences of any 10 or more contiguous nucleotides within a sequence from SEQ ID NOS: 1-27 listed in Table 1. Alternatively, as detailed earlier, the sequence that encodes for the effector sequence or the sequence complementary to the first effector sequence may vary from SEQ ID NOS: 1-27 by 1, 2, 3, 4 or 5 nucleotides without affecting the ability of the sequence encoded to base pair with the target sequence and inhibit expression of the HBV target sequence.

Typically, each effector sequence forms a double stranded region with the corresponding effector complement sequence.

In an alternative embodiment, the method of treating HBV infection in an individual comprises the administration of a therapeutically effective amount of a ddRNAi construct that encodes a ddRNAi agent having more than one effector sequence, such as those listed above.

The HBV infection to be treated may be a chronic HBV infection. By "chronic" it is meant that the infection with HBV is long-lasting or persistent. The term chronic describes the course of the disease, or its rate of onset and development. When treating chronic HBV infection, it is preferable that the ddRNAi construct is administered and either stably maintained or integrated in to the target cell to ensure longer term expression of the ddRNAi agent. As detailed above, this can be achieved with the use of a ddRNAi construct having a viral vector backbone. In accordance with this, there is provided a method of treating chronic HBV infection in an individual comprising the administration of a therapeutically effective amount of a ddRNAi construct of the invention to a patient in need of treatment.

Treatment of chronic HBV infection is aimed at reducing the infectivity of the virus by interfering with viral replication. This in turn lowers the risk of transmission and spread of HBV. There is therefore provided a method of reducing the infectivity of HBV in an individual infected with HBV, comprising administering to the individual a ddRNAi constructs of the invention to target a HBV gene, preferably the polymerase gene. The clinical endpoints used in chronic hepatitis B therapy will differ between patients with compensated hepatitis B (where sustained viral suppression, serological response, histological improvement, normalisation of liver function tests and non-clinical progression are key endpoints) and those with decompensated hepatitis B. In patients with decompensated disease the liver is extensively scarred and fibrotic and prevention/reversal of liver damage and prevention of disease progression and obviation of liver transplantation are the main objectives of therapy. Endpoints for compensated hepatitis B are reduction of viral load with serological and biochemical improvement, histological improvement, measure of liver failure and end stage liver disease, complications, transplantation and mortality.

In another embodiment, there is provided a method of minimising progression of liver disease in a subject as a result of HBV infection, comprising administering to the individual a ddRNAi construct of the invention to target a HBV gene, preferably the polymerase gene.

In yet another embodiment of the invention, there is provided a method of minimising the symptoms associated with HBV infection in a subject, comprising administering to the individual a ddRNAi construct of the invention to target a HBV gene, preferably the polymerase gene.

The status or severity of an individual's HBV infection may be assessed by determining their viral load. By "viral load" it is meant the amount of virus in an involved body fluid. For example, it can be given in RNA copies per milliliter of blood plasma. Individuals having a high viral load are considered to have a more severe HBV infection. Alternatively, the viral load is an indicator of the responsiveness of an individual to a particular treatment. If a treatment is working and keeping the levels of virus low, it is indicative of a successful treatment. It is therefore an objective of treatment to lower an individual's viral load. Accordingly, there is also a provided a method of lowering a viral load of an individual with an HBV infection, comprising administering to the individual a ddRNAi construct of the invention to target a HBV gene, preferably the polymerase gene.

Subsequent monitoring of the viral load in the individual who has received treatment with a ddRNAi construct of the invention is therefore a phenotypic indicator of the effectiveness of the ddRNAi construct and the ddRNAi agent of the invention.

Alternatively, treatment of acute HBV infection may not require long term treatment, and it may in fact be preferred to rely on the transient presence of a ddRNAi agent or siRNA agent as opposed to long term expression of ddRNAi agents from integrated or stably maintained ddRNAi constructs. By "acute" it is meant that the HBV infection has a rapid onset, and/or a short duration.

In accordance with this embodiment of the invention, there is provided a method of treating acute HBV infection in an individual comprising the administration of a therapeutically effective amount of an in vitro synthesised or chemically synthesised ddRNAi agent to a patient in need of treatment, for inhibiting expression of one or more target sequences in a Hepatitis B virus (HBV) gene, the ddRNAi agent comprising at least:

a first effector sequence of at least 17 nucleotides in length selected from any 10 or more contiguous nucleotides within a sequence from the group consisting of SEQ ID NOS: 1-27; and a first effector complement sequence;

wherein the effector sequence is substantially complementary to the predicted transcript of a region of the target gene. In this embodiment, the ddRNAi agent of the invention is produced in vitro or chemically synthesised and provided to the cell.

Any of the siRNA agents or ddRNAi agents of the invention described throughout the specification are suitable for in vitro expression and delivery to the cell.

Preferably, the HBV target gene is at least the polymerase (P) gene, and potentially the surface antigen, core antigen or X gene when the target sequence is contained within overlapping open reading frames. Accordingly, in one embodiment of the invention, the ddRNAi agent inhibits expression of one or more target sequences in a Hepatitis B virus (HBV) polymerase gene. The first effector sequence is preferably selected from any 10 or more and preferably any 17 or more contiguous nucleotides within a sequence from the effector sequences SEQ ID NOS: 1-27 listed in Table 1. Alternatively, the effector sequence may vary from SEQ ID NOS: 1-27 by 1, 2, 3, 4 or 5 nucleotides without affecting the ability of the effector sequence to base pair with the target sequence and inhibit expression of the HBV polymerase gene.

In an alternative embodiment, an siRNA agent may be administered. Preferably the siRNA agents, similarly to the ddRNAi agent, targets the HBV polymerase gene, and may have a sequence selected from any 10 or more and preferably any 17 or more contiguous nucleotides within a sequence from the group consisting of SEQ ID NOS: 1-27, or may vary from SEQ ID NOS: 1-27 by 1, 2, 3, 4 or 5 nucleotides without affecting the ability of the effector sequence to base pair with the target sequence and inhibit expression of the HBV polymerase gene.

Administration of a ddRNAi agent or siRNA agent of the invention to an individual with an acute HBV infection can also lower a viral load, reduce the severity of symptoms associated with the acute infection, and reduce the infectivity of HBV.

In another aspect of the invention, there is provided the use of the ddRNAi constructs, ddRNAi agents or siRNA agents of the invention in the preparation of medicaments for treatment of HBV infection, preferably chronic HBV infection, the reduction of HBV viral load, the reduction of the severity of symptoms associated with HBV infection, and the reduction of the infectivity of HBV.

In a further aspect of the invention there is provided ddRNAi constructs, ddRNAi agents or siRNA agents for treating HBV infection, preferably chronic HBV infection, reducing HBV viral load, reducing the severity of symptoms associated with HBV infection, and reducing the infectivity of HBV.

In a further aspect of the invention there is provided a composition comprising ddRNAi constructs, ddRNAi agents or siRNA agents as an active ingredient for treating HBV infection, preferably chronic HBV infection, reducing HBV viral load, reducing the severity of symptoms associated with HBV infection, and reducing the infectivity of HBV.

The one or more effector sequences of the ddRNAi constructs, ddRNAi agents or siRNA agents used in the methods of the invention comprise any 10 or more, preferably any 17 or more, contiguous nucleotides within sequences able to inhibit the expression of the HBV target gene region by at least 70%. Preferably the one or more effector sequence is selected from SEQ ID NO:3, SEQ ID NO:9, SEQ ID NO:12, SEQ ID NO:13 and SEQ ID NO:23.

Pharmaceutical Compositions

The ddRNAi agents, the siRNA agents or the vectors comprising ddRNAi expression cassettes of the invention can be formulated into pharmaceutical compositions by combination with appropriate, pharmaceutically acceptable carriers or diluents. Accordingly, there is provided a pharmaceutical composition comprising a ddRNAi agent, a ddRNAi expression cassette, a ddRNAi construct or a siRNA agent of the invention and a pharmaceutically acceptable carrier or diluent.

In pharmaceutical dosage forms, the agents or the vectors comprising the ddRNAi expression cassettes may be administered alone or in association or combination with other pharmaceutically active compounds. Those with skill in the art will appreciate readily that dose levels for agents or vectors comprising the ddRNAi expression cassettes will vary as a function of the nature of the delivery vehicle, the relative ease of transduction of the target cells, the expression level of the RNAi agents in the target cells and the like.

The ddRNAi agents, the siRNA agents or the vectors comprising ddRNAi expression cassettes of the invention can be formulated into preparations for injection or administration by dissolving, suspending or emulsifying them in an aqueous or non aqueous solvent, such as oils, synthetic aliphatic acid glycerides, esters of higher aliphatic acids or propylene glycol; and if desired, with conventional additives such as solubilisers, isotonic agents, suspending agents, emulsifying agents, stabilizers and preservatives.

Pharmaceutically acceptable carriers or diluents contemplated by the invention include any diluents, carriers, excipients, and stabilizers that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as plasma albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The pharmaceutical composition may be prepared for various routes and types of administration. In general the formulations are prepared by uniformly and intimately bringing into association the active ingredient with liquid carriers or finely divided solid carriers or both, and if necessary, shaping the product. Formulation may be conducted by mixing at ambient temperature at the appropriate pH, and at the desired degree of purity, with physiologically acceptable carriers, i.e., carriers that are non-toxic to recipients at the dosages and concentrations employed.

The one or more effector sequences of the ddRNAi constructs, ddRNAi agents or siRNA agents used in the compositions of the invention comprise any 10 or more, preferably any 17 or more, contiguous nucleotides within sequences able to inhibit the expression of the HBV target gene region by at least 70%. Preferably the one or more effector sequence is selected from SEQ ID NO:3, SEQ ID NO:9, SEQ ID NO:12, SEQ ID NO:13 and SEQ ID NO:23.

EXAMPLES

The following examples are illustrative in nature and are in no way intended to be limiting.

Example 1: Production of an Entire siRNA Target (EsT) Library

Figure 2:
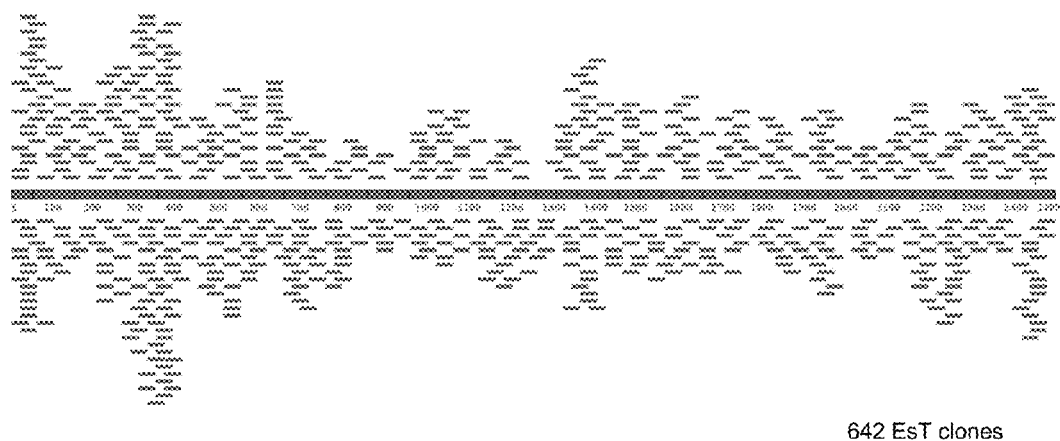
FIG. 2 shows the distribution of the 642 siRNA clones obtained along the HBV polymerase gene, wherein the lines denote regions corresponding to individual Entire siRNA Target (EsT) clones.

The full length HBV RNA-dependent DNA polymerase gene from HBV Adr-1 (Accession M38454) was sub-cloned and used to generate an Entire siRNA Target (EsT) library. 5000 clones were sequenced, of which 642 were identified as having non-repeat sequences ranging from 19-23 bp. The sequences, which represent potential targets for the ddRNAi agents of the invention, were distributed along the target gene (FIG. 2).

Example 2: Large Scale Screening Results Using SECs with ≥50% Knock Down

To identify the most effective siRNA sequences which could then be used to prepare the ddRNAi agents of the invention, siRNA expression cassettes (SECs) amplified by PCR were transfected into HepG2 2.2.15 cells. Effects on the levels of HBV polymerase mRNA expression was evaluated to identify functional siRNA sequences.

Figure 3:
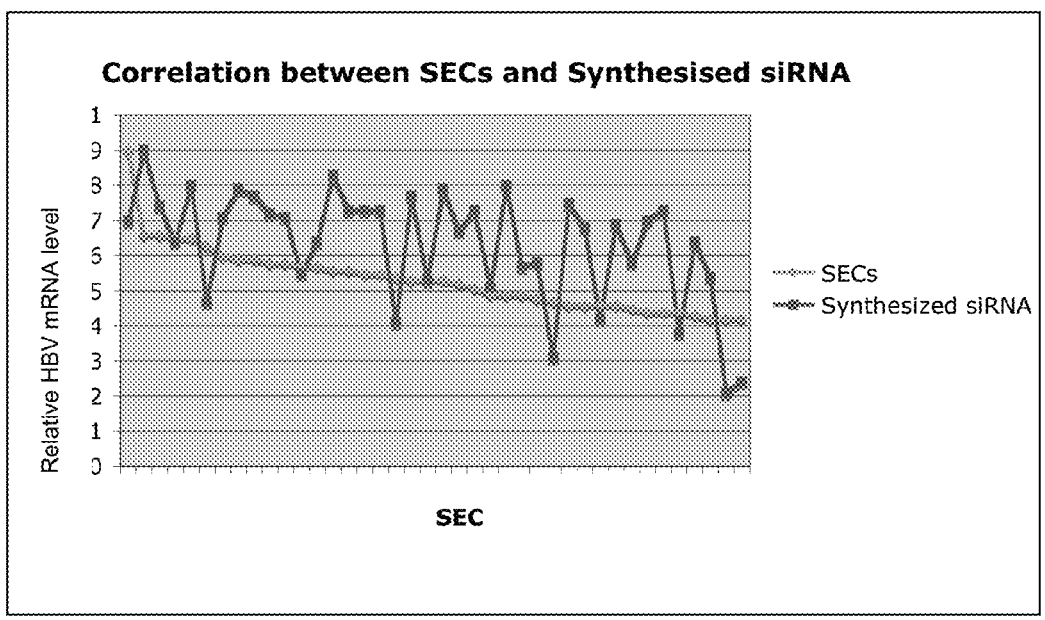
FIG. 3 is a comparison of the RNAi effectiveness of siRNA expression cassettes (SECs) and their corresponding synthetic siRNAs on HBV polymerase mRNA levels in order to validate the initial screening results obtained with SEC inhibition of HBV polymerase expression3.

40 siRNAs that corresponded to the first SECs screened were chemically synthesised and transfected into HepG2 2.2.15 cells to validate the original polymerase mRNA knock down levels. HepG2 2.2.15 is a stable cell line containing an integrated tandem dimer of the HBV genome (Genebank Accession #: U95551), and can stably express HBV antigens and HBV Dane particles. The correlation results are shown in FIG. 3.

As can be seen from FIG. 3, when SECs inhibition of polymerase expression was >50%, most of the corresponding synthetic siRNA sequences gave around 70% knockdown of HBV mRNA, and only 2/23 gave knockdown levels below 50%. In contrast to the SECs with <50%, silencing efficiency, only 18% (3/17) of the corresponding synthetic siRNAs produced >70% knock down (p<0.05—Pearson's chi-square test, |t Stat|=4.29>1.68). Furthermore, a synthetic siRNA (need explanation of this) which produced >90% knock down corresponded to a SEC clone which gave >65% knock down. From this it was concluded that a reasonable correlation existed between the knock down of HBV mRNA by siRNA from SECs and that produced by synthetic siRNAs, to a cut-off value of ≥50% knock down by SECs. This cut off value was used for the rest of the screening of the SECs.

Example 3: Target Screening by siRNA Expression Cassettes (SECs)

FIG. 4 shows the results of large scale screening in vitro for inhibition of HBV mRNA accumulation (501 non-repeated siRNA agents). Of those sequences screened, 100 siRNA sequences were effective in knocking down HBV mRNA by ≥50%, 14 of which resulted in >70% knock down (Table 2). The distribution of the top 100 siRNA targets on the HBV polymerase gene is shown in FIG. 5A; any sequence can in turn be mapped on the polymerase. FIG. 5B for example maps the first 3 sequences.

TABLE 2

| SEQ ID NO | RNAi effector sequence <sup>a</sup> | Length (bp) | Relative mRNA expression |
|---|---|---|---|
| 1 | GAUUGACGAUAAGGGAGA | 18 | 0.1 |
| 2 | UUGAAGUCCCAAUCUGGAU | 19 | 0.14 |
| 3 | GCCGGGCAACGGGGUAAAGGUUC | 23 | 0.19 |
| 4 | UAUUUGCGGGAGAGGACAACAGAGUUAUC | 29 | 0.25 |
| 5 | UCCUGAUGUGAUGUUCUCCAUGU | 23 | 0.25 |
| 6 | AAGGCCUCCGUGCGGUGGGG | 20 | 0.26 |
| 7 | GGUAUUGUUUACACAGAAAGGC | 22 | 0.26 |
| 8 | GAUGUGUUCUUGUGGCAAG | 19 | 0.27 |
| 9 | GGGAAAGCCCUACGAACCACU | 21 | 0.27 |
| 10 | GUGGAGACAGCGGGGUAGGC | 20 | 0.28 |
| 11 | GAGGACAACAGAGUUAUC | 18 | 0.29 |
| 12 | GCCCACUCCCAUAGGAAUUUUCC | 23 | 0.29 |
| 13 | GGAUCUUGCAGAGUUUGG | 18 | 0.29 |
| 14 | CGUUGCCGGGCAACGGGGUA | 20 | 0.29 |

Relative mRNA expression was measured (by a one-step quantitative RT-PCR method using SensiMix SYBR One-Step Kit (Bioline, USA) according to the manufacturer's guidelines) in transfected HepG2 2.2.15 cells relative to an empty vector control whose level was arbitrarily set at 1.0. The specific primers for the HBV polymerase gene were forward primer 5'-TGTGGTTATCCTGCGTTAATG-3' Reverse primer 5'-GCGTCAGCAAACACTTGG-3', the PCR product was 158 bp long. U6 snRNA (forward primer 5'-CTCGCTTCGGCAGCACA-3' Reverse primer 5'-AACGCTTCACGAATTTGCGT-3') was used as the internal control, the PCR product was 94 bp long. The relative expression level of Polymerase gene was normalized using the 2-ΔΔCt analysis method. The experiments were performed using quadruplicate independent transductions.

Example 4: Confirmation of Activity Using Synthesised siRNAs

The first round of screening used a vector with opposing promoters (pU6H1-GFP). In shRNA expressing constructs the shRNA is under the control of a single promoter. Accordingly, to confirm the efficacy of the top 14 siRNA sequences shown in Table 2 prior to developing shRNA expression constructs based on them, HepG2 2.2.15 cells were transfected with each siRNA and inhibition of HBV replication was assayed to determine HBV polymerase mRNA levels.

The 14 siRNAs were chemically synthesized with a dTdT 3' overhang. 5'-FAM labelled siRNA-GL3 (pGL3 Luciferase Reporter Vector with unrelated siRNA sequence) served as negative control. The siRNAs were dissolved in 100 uM in DEPC-treated water, aliquoted out and stored at −20° C. In addition, SEQ ID NO:4, which is 29 bp long, was redesigned into 8 siRNAs (SEQ ID NOS:20 to 27), each of 22 bp made up of overlapping sequence from SEQ ID NO:4 (Table 3 below):

TABLE 3

| SEQ ID NO | RNAi effector sequence |
|---|---|
| 4 | UAUUUGCGGGAGAGGACAACAGAGUUAUCTT |
| 20 | GGGAGAGGACAACAGAGUUAUCTT |
| 21 | CGGGAGAGGACAACAGAGUUAUTT |
| 22 | GCGGGAGAGGACAACAGAGUUATT |
| 23 | UGCGGGAGAGGACAACAGAGUUTT |
| 24 | UUGCGGGAGAGGACAACAGAGUTT |
| 25 | UUUGCGGGAGAGGACAACAGAGTT |
| 26 | AUUUGCGGGAGAGGACAACAGATT |
| 27 | UAUUUGCGGGAGAGGACAACAGTT |

Transfection optimization was performed by varying 5' FAM-labelled siRNA-GL3 and Lipofectamine 2000 (Invitrogen). The cells were maintained in DMEM (GIBCO, USA) supplemented with 10% PBS (Excellbio, China) and 200 μg/mL G418 (Sangon, China) at 37° C., 5% CO2.

HepG2 2.2.15 cells were transfected with siRNAs using the optimised protocol and harvested 72 h after transfection. Total RNA was isolated using Trizol (Invitrogen) and quantified in a one-step quantitative RT-PCR method using SensiMix SYBR One-Step Kit (Bioline, USA) according to the manufacturer's guidelines as already detailed in Example 3.

Results

The results are expressed as mean±STDV (Table 4 and FIG. 9).

| SEQ ID NO | Polymerase mRNA Level | | | | | |
|---|---|---|---|---|---|---|
| | Lot 1 | Lot 2 | Lot 3 | Lot 4 | AVERAGE | STDV |
| 1 | 0.39 | 0.52 | 0.51 | 0.72 | 0.54 | 0.1373 |
| 2 | 0.79 | 0.24 | 0.18 | 0.43 | 0.41 | 0.2722 |
| 3 | 0.58 | 0.27 | 0.18 | 0.14 | 0.29 | 0.2014 |
| 4 | | 0.41 | 0.34 | 0.22 | 0.33 | 0.0928 |
| 5 | 0.34 | 0.35 | 0.44 | 0.37 | 0.37 | 0.0450 |
| 6 | 0.36 | 0.32 | 0.26 | 0.54 | 0.37 | 0.1190 |
| 7 | 0.45 | 0.30 | 0.26 | 0.63 | 0.41 | 0.1702 |
| 8 | 0.48 | 0.46 | 0.33 | 0.72 | 0.50 | 0.1653 |
| 9 | 0.45 | 0.26 | 0.20 | 0.28 | 0.30 | 0.1068 |
| 10 | 0.17 | 0.40 | 0.43 | 0.67 | 0.42 | 0.2053 |
| 11 | 0.32 | 0.33 | 0.30 | 0.30 | 0.31 | 0.0178 |
| 12 | 0.32 | 0.28 | 0.16 | 0.26 | 0.25 | 0.0704 |
| 13 | 0.23 | 0.25 | 0.23 | 0.26 | 0.24 | 0.0152 |
| 14 | 0.36 | 0.34 | 0.38 | 0.36 | 0.36 | 0.0180 |
| 20 | 0.43 | 0.23 | 0.19 | 0.30 | 0.29 | 0.1027 |
| 21 | 0.33 | 0.40 | 0.24 | 0.19 | 0.29 | 0.0915 |
| 22 | 0.37 | 0.51 | 0.84 | 0.27 | 0.50 | 0.2453 |
| 23 | 0.18 | 0.29 | 0.20 | 0.32 | 0.25 | 0.0648 |
| 24 | 0.31 | 0.38 | 0.46 | 0.45 | 0.40 | 0.0686 |
| 25 | 0.50 | 0.33 | 0.54 | 0.25 | 0.41 | 0.1400 |
| 26 | 0.43 | 0.41 | 0.32 | 0.43 | 0.40 | 0.0518 |
| 27 | 0.38 | 0.44 | 0.33 | 0.31 | 0.37 | 0.0585 |
| siNC | 0.72 | 0.73 | 0.69 | 0.78 | 0.73 | 0.0398 |
| Normal | 1.00 | 1.00 | 1.00 | 1.00 | 1.00 | 0.0000 | siNC = negative control;
Normal = untransfected cells

Of the 22 siRNAs tested, all exhibited at least about 50% inhibition, and most exhibited 60 to 70% inhibition. Despite the high sequence similarity between the 22 bp variants SEQ ID NO: 20 to 27 of SEQ ID NO:4, the ability to inhibit expression of their sequence varied from 50 to 71%. Based on these results, SEQ ID NOS: 3, 9, 12, 13 and 23 were selected for further development. While all of those SEQ ID NOS target the polymerase gene, these sequences were also selected on the basis of their spread along the polymerase gene mRNA (see column "HBV Target Sites" in Table 1).

Example 5: shRNA Design and Construction

Step 1—Effector Sequence Design shRNA expression constructs were designed based on SEQ ID NOS: 3. 9, 12, 13 and 23. Constructs can be readily synthesised using a variety of promoters, including different versions of human U6 promoters with different intrinsic activities (Domitrovich, A M and Kunkel, G R (2003) Multiple, dispersed human U6 small nuclear RNA genes with varied transcriptional efficiencies *Nucleic Acids Research* 31: 2344-2352) or various pol II promoters. In designing these constructs, the following considerations were applied:

Dicer processes from the base of shRNAs
  Dicer processing is imprecise but is predominantly expected to cut every 22 nucleotides
U6 termination is expected to add a UU to the 3' end to the shRNA
the processed effector sequence desirably contains a 5' U or A to facilitate efficient Ago 2 loading.
the effector sequence is positioned 3' of the loop to avoid the 5' G preferred for maximal U6 transcription
5' A or U residues can be incorporated into shRNA effector sequences by incorporating sequences 2 or 3 nucleotides upstream or downstream of the sequences targeted by the RNAi agent; this is referred to as "sliding" sequences 1, 2 or 3 nucleotides ie the effector sequence for shRNAs can be based on sequences 1, 2 or 3 nucleotides 5' or 3' relative to the 5' end of the siRNA effector sequence.

When applied to the 5 siRNAs based on SEQ ID NOS: 3. 9, 12, 13 and 23:

i) For a shRNA based on SEQ ID NO:3: gccgggcaacggggtuaaagguucTT

"Best" shRNA effector sequence (minimize 5' GC sequences, slide "down" 3 nts)

GGGCAACGGGGUAAAGGUUCuu (uu from pol III termination)

ii) For a shRNA based on SEQ ID NO:9: gggaaagcccuacgaaccacuTT

"Best" shRNA effector sequence (minimize 5' Gs, slide down 3 nts to 5' A, add GA to 3' (from HBV genome to maximize homology)

AAAGCCCUACGAACCACUGAuu iii) For a shRNA based on SEQ ID NO:12: gcccacucccauaggaauuuuccTT "Best" shRNA effector sequence move up 2 nts to avoid UUUU (will cause premature termination) on antisense strand, add AG from HBV sequence, which fortuitously incorporates a 5' A.

AGGCCCACUCCCAUAGGAAUU iv) For a shRNA based on SEQ ID NO:13: ggaucuugcagaguuuggTT "Best" shRNA effector sequence (increase length to 20 nts, slide up 2 nts, add TG from HBV sequence, which results in a 5' T (ie U)

TGGGAUCUUGCAGAGUUUGGuu v) For a shRNA based on SEQ ID NO:23: ugcgggagaggacaacagaguuTT "Best" shRNA effector sequence reduce size at 3' end by 2 nts

UGCGGGAGAGGACAACAGAGUU

Step 2—Expression Cassette

U6 shRNA cassettes (Genscript) based on the effector sequences designed in step (a) were prepared and cloned in to pUC57.

The inserts of the expression cassettes, which included some flanking restriction sites for subsequent manipulation, had the following sequences:

U6.HBVshRNA 3
(SEQ ID NO: 28)
GGGACCCGGTACCTCGAGAGATCTGGGCAGGAAGAGGGCCTATTTCCCAT

GATTCCTTCATATTTGCATATACGATACAAGGCTGTTAGAGAGATAATTA

GAATTAATTTGACTGTAAACACAAAGATATTAGTACAAAATACGTGACGT

AGAAAGTAATAATTTCTTGGGTAGTTTGCAGTTTTAAAATTATGTTTTAA

AATGGACTATCATATGCTTACCGTAACTTGAAAGTATTTCGATTTCTTGG

CTTTATATATCTTGTGGAAAGGACGAAACACCGAACCTTTACCCCGTTGC

CCGGCAAGAGACCGGGCAACGGGGTAAAGGTTCTTTTTTGTTAACGAAT

TC

U6.HBVshRNA 9
(SEQ ID NO: 29)
GGGACCCGGTACCTCGAGAGATCTGGGCAGGAAGAGGGCCTATTTCCCA

TGATTCCTTCATATTTGCATATACGATACAAGGCTGTTAGAGAGATAAT

TAGAATTAATTTGACTGTAAACACAAAGATATTAGTACAAAATACGTGA

CGTAGAAAGTAATAATTTCTTGGGTAGTTTGCAGTTTTAAAATTATGTT

TTAAAATGGACTATCATATGCTTACCGTAACTTGAAAGTATTTCGATTT

CTTGGCTTTATATATCTTGTGGAAAGGACGAAACACCGTCAGTGGTTCG

TAGGGCTTTCCCAAGAGAGGAAAGCCCTACGAACCACTGATTTTTTGTT

AACGAATTC

U6.HBVshRNA 12
(SEQ ID NO: 30)
GGGACCCGGTACCTCGAGAGATCTGGGCAGGAAGAGGGCCTATTTCCCA

TGATTCCTTCATATTTGCATATACGATACAAGGCTGTTAGAGAGATAAT

TAGAATTAATTTGACTGTAAACACAAAGATATTAGTACAAAATACGTGAC

GTAGAAAGTAATAATTTCTTGGGTAGTTTGCAGTTTTAAAATTATGTTTT

AAAATGGACTATCATATGCTTACCGTAACTTGAAAGTATTTCGATTTCTT

-continued
```
GGCTTTATATATCTTGTGGAAAGGACGAAACACCGATTCCTATGGGAGTG

GGCCTCACAAGAGATGAGGCCCACTCCCATAGGAATTTTTTGTTAACGA

ATTC
```

U6.HBVshRNA 13
(SEQ ID NO: 31)
```
GGGACCCGGTACCTCGAGAGATCTGGGCAGGAAGAGGGCCTATTTCCCA

TGATTCCTTCATATTTGCATATACGATACAAGGCTGTTAGAGAGATAAT

TAGAATTAATTTGACTGTAAACACAAAGATATTAGTACAAAATACGTGA

CGTAGAAAGTAATAATTTCTTGGGTAGTTTGCAGTTTTAAAATTATGTT

TTAAAATGGACTATCATATGCTTACCGTAACTTGAAAGTATTTCGATT

TCTTGGCTTTATATATCTTGTGGAAAGGACGAAACACCGCCAAACTCT

GCAAGATCCCAGACAAGAGATCTGGGATCTTGCAGAGTTTGGTTTTTG

TTAACGAATTC
```

U6.HBVshRNA 23
(SEQ ID NO: 32)
```
GGGACCCGGTACCTCGAGAGATCTGGGCAGGAAGAGGGCCTATT

TCCCATGATTCCTTCATATTTGCATATACGATACAAGGCTGTTA

GAGAGATAATTAGAATTAATTTGACTGTAAACACAAAGATATTA

GTACAAAATACGTGACGTAGAAAGTAATAATTTCTTG

TTGAAAGTATTTCGATTTCTTGGCTTTATATATCTTGTGGAAAGG

ACGAAACACCGCTCTGTTGTCCTCTCCCGCAAACAAGAGATTTGC

GGGAGAGGACAACAGAGTTTTTGTTAACGAATTC
```

The corresponding expressed shRNA for each of these expression cassettes are shown in FIG. 6 (as SEQ ID NOS: 36 to 40). Symbol "∧" and "∨" indicates potential processing sites of shRNA, resulting from either transcriptional initiation/termination or Dicer processing with a 22 nt phase and 2 nt 3' overhang, the predicted effector sequence assuming such processing is shown below.

Example 6: Generation of Stable shRNA Expressing Cells Using Multiple Sequence Constructs As outlined above, one useful way of designing ddRNAi expression cassettes of the invention is to assume Dicer cuts every 22 nucleotides (also referred to as 22 nt phasing). The DNA sequences that encode effector sequences can therefore be designed to encode any 10 or more, and preferably any 17 or more contiguous nucleotides within a sequence from the group consisting of SEQ ID NOS:1-27, together with appropriate spacers and other sequence requirements for the promoter and/or terminator.

ddRNAi constructs will be generated with the following structures (using non-limiting exemplary sequences):
i) Single Hairpin Expression Cassette
As mentioned above, FIG. 6 illustrates the expression cassette, expressed hairpin RNAi agent and theoretical effector sequence processed by Dicer (assuming 22 nucleotide phasing) based on SEQ ID NO: 3 (FIG. 6A), SEQ ID NO:9 (FIG. 6B) and SEQ ID NO:12 (FIG. 6C), SEQ ID NO: 13 (FIG. 6D) and SEQ ID NO: 23 (FIG. 6E). In the cassette of FIGS. 6A and 6B, 20 contiguous nucleotides of SEQ ID NO:3 and 9 respectively are encoded for; in the cassette of FIG. 6C to 6E, 21 contiguous nucleotides of SEQ ID NO: 12, 13 and 23 respectively are encoded for. The arrows on the hairpin RNAi agent indicate where Dicer is expected to cut to produce the effector sequence shown underneath.

The sequence of the expression cassettes of FIGS. 6A to 6E have already been provided above (SEQ ID NOS: 28 to 32).

ii) Multiple Hairpin Expression Cassette

FIG. 7 illustrates the expression cassette, expressed hairpin RNAi agent (SEQ ID NOS: 41 to 43 and theoretical effector sequence processed by Dicer (assuming 22 nucleotide phasing) based on SEQ ID NO: 1, SEQ ID NO:4 and SEQ ID NO:6 when arranged within the cassette to give rise to expression of individual hairpin RNAi agents (FIG. 7A) or a single RNA containing the 3 hairpin RNAi agents prior to processing (FIG. 7B). SEQ ID NOS:1, 4 and 6 are the same as described above in relation to the single hairpin expression cassette. The "∧" and "∨" symbols on the hairpin RNAi agent indicate where Dicer is expected to cut to produce the effector sequence shown underneath.

The expression cassette of FIG. 7A has a DNA sequence of (SEQ ID NO: 33)
```
TACAAAATACGTGACGTAGAAAGTAATAATTTCTTGGGTAGTTTG

CAGTTTTAAAATTATGTTTTAAAATGGACTATCATATGCTTACCG

TAACTTGAAAGTATTTCGATTTCTTGGCTTTATATATCTTGTGGA

AAGGACGAAACACCGTCTCCCTTATCGTCAATCTTCAAGAGAAAG

ATTGACGATAAGGGAGATTTTTTTACAAAATACGTGACGTAGAA

AGTAATAATTTCTTGGGTAGTTTGCAGTTTTAAAATTATGTTTTA

AAATGGACTATCATATGCTTACCGTAACTTGAAAGTATTTCGATT

TCTTGGCTTTATATATCTTGTGGAAAGGACGAAACACCGATAACT

CTGTTGTCCTCTTTCAAGAGAAGAGGACAACAGAGTTATCTTTTT

TTTACAAAATACGTGACGTAGAAAGTAATAATTTCTTGGGTAGTT

TGCAGTTTTAAAATTATGTTTTAAAATGGACTATCATATGCTTAC

CGTAACTTGAAAGTATTTCGATTTCTTGGCTTTATATATCTTGTG

GAAAGGACGAAACACCGCCCCACCGCACGGAGGCCTTTTCAAGAG

AAAGGCCTCCGTGCGGTGGGGTTTTTTT.
```

In the cassette of FIG. 7A each effector complement is operably linked to a promoter sequence, and the corresponding effector sequence is operably linked to termination elements or sequences.

In contrast, in the expression cassette of FIG. 7B the first effector complement (effector 1 comp) is operably linked to a promoter and the last effector (effector 6) is operably linked to a terminator element or sequence, arrows indicate anticipated sites for Dicer processing. This cassette is designed to express a single RNA molecule (SEQ ID NO: 44), and has a DNA sequence of (SEQ ID NO: 34)
```
TACAAAATACGTGACGTAGAAAGTAATAATTTCTTGGGTAGTTT

GCAGTTTTAAAATTATGTTTTAAAATGGACTATCATATGCTTAC

CGTAACTTGAAAGTATTTCGATTTCTTGGCTTTATATATCTTGT

GGAAAGGACGAAACACCGTGCTGTTGACAGTGAGCGTCTCCCTT

ATCGTCAATCTTCAAGAGAAAGATTGACGATAAGGGAGATGCCT
```

-continued

```
ACTGCCTCGGATTCTGCTGTTGACAGTGAGCGGTTGTCCTCTCC

CGCAAATACAAGAGATATTTGCGGGAGAGGACAACTGCCTACTG

CCTCGGATTCTGCTGTTGACAGTGAGCGCCCCACCGCACGGAGG

CCTTCAAGAGAAAGGCCTCCGTGCGGTGGGGTGCTGTTGACAGT

GAGCGTTTTTT.
``` iii) Long Hairpin Expression Cassette

FIG. 8 illustrates the expression cassette, expressed hairpin RNAi agent (SEQ ID NO: 45) and theoretical effector sequence processed by Dicer (assuming 22 nucleotide phasing) based on (in order) SEQ ID NO: 1, SEQ ID NO:6 and SEQ ID NO:4. In the cassette of FIG. 8, 17 contiguous nucleotides of SEQ ID NO:1 are encoded for and 20 contiguous nucleotides of SEQ ID NO:6 as per the above examples, but in contrast to the cassettes of FIGS. 7 and 8, only 18 contiguous nucleotides of SEQ ID NO:4 are encoded for. The arrows on the hairpin RNAi agent indicate where Dicer is expected to cut to produce the effector sequence shown underneath.

The expression cassette of FIG. 8 has a DNA sequence of

```
                                        (SEQ ID NO: 35)
TACAAAATACGTGACGTAGAAAGTAATAATTTCTTGGGTAGTT

TGCAGTTTTAAAATTATGTTTTAAAATGGACTATCATATGCTT

ACCGTAACTTGAAAGTATTTCGATTTCTTGGCTTTATATATCT

TGTGGAAAGGACGAAACACCGCTCCCTTATCGTCAATCTTCAC

CCCACCGCACGGAGGCCTTCTGATGTCCTCTCCCGCAAATACA

AGAGATATTTGCGGGAGAGGACAACAGAAGGCCTCCGTGCGGT

GGGGTGAAAGATTGACGATAAGGGAGATTTTTTT.
```

Example 7: Assaying the Effectiveness of ddRNAi Agents In Vitro

To test the efficacy of ddRNAi agents appropriate cells and cell lines can be transfected with RNA agents of the invention and inhibition of HBV replication assayed To assay the efficacy of ddRNAi constructs of the invention, plasmid DNAs based on the pGL3 Luciferase Reporter Vector were constructed. The first, "pGL3 multi" contains single copies of sequence in the 3' untranslated regions (UTR) of the firefly luciferase expressing plasmid pGL3, encoding target sites for siRNA or shRNA 3, 9, 12, 13 and 23, based on SEQ ID NOS: 3. 9, 12, 13 and 23 respectively. The second, "pGL3-23" contains a triple repeat of shRNA 23, based on SEQ ID NO:23. The HBV target sites in these plasmids correspond to the sense sequences of HBV recognised by particular siRNAs or shRNAs and include an additional 10 nts of HBV sequence upstream and downstream of the target sites.

The following information relates to experiments conducted using the pGL3-23 construct.

For convenience we chose to undertake initial testing using dual-luciferase assays with transient assays in HEK293 cells. Cells were plated in 96-well plates (0.1 ml medium/well) to reach about 50% confluence before transfection. Plasmid DNAs and the chemical synthesized siRNAs (or shRNA vectors) were co-transfected into HEK293 cells with Lipofectamine™ 2000 using the manufacturer's (Invitrogen) protocol. The test constructs were used together with a construct expressing Renilla luciferase (pRL-TK, Promega) which acts an internal control for transfection efficiency.

If the chemically synthesized siRNAs, or shRNA expressed from vectors are effective at silencing the target sequence, luciferase levels in transfected cells will be decreased since the target sequences are operably linked to the luciferase gene.

Accordingly, various amounts of chemically synthesized siRNAs or shRNA expression vectors were co-transfected with constant amounts of pGL3-23 and control plasmids (see Tables below).

TABLE 5

Testing siRNA23 against pGL3-23

| pGL3-23(ng) | pRL-TK(ng) | siRNA | | siNC (pmol) |
|---|---|---|---|---|
| 20 | 2 | siNC | 0 | 10.0 |
| | | HBV-siRNA23 | 0.5 | 9.5 |
| | | | 1.0 | 9.0 |
| | | | 2.5 | 7.5 |
| | | | 5.0 | 5.0 |
| | | | 10.0 | 0.0 |
| | | siRNA-GL3 | 5.0 | 5.0 |

Cells were transfected with indicated amounts of pGL3-23 and control (pRL-TK) plasmids and varying amounts of siRNAs based on SEQ ID NO:23 (HBV-siRNA23). siNC, an unrelated siRNA with no known target sequences in HBV, was used both as a negative control and to adjust total quantities of siRNAs added to cells to avoid potential artifacts due to unequal transfection. siRNA GL3 was used as a positive control, such that it is an siRNA targeted to the luciferase gene.

TABLE 6

Testing shRNA23 against pGL3-23

| pGL3-23(ng) | pRL-TK (ng) | shRNA (ng) | | pUC57 (ng) |
|---|---|---|---|---|
| 20 | 2 | pUC57 | 0 | 100 |
| | | HBV shRNA23 | 2 | 98 |
| | | | 5 | 95 |
| | | | 10 | 90 |
| | | | 20 | 80 |
| | | | 50 | 50 |
| | | | 100 | 0 |
| | | U6 shRNA-GL3 | 50 | 50 |

Cells were transfected with indicated amounts of pGL3-23 and control (pRL-TK) plasmids and varying amounts of test plasmid for expressing shRNA based on SEQ ID NO:23 (HBV shRNA23). pUC57 was used both as a negative control and to adjust total quantities of plasmid DNAs added to cells to avoid potential artifacts due to unequal transfection. A plasmid expressing a luciferase shRNA based on GL3 siRNA was used as a positive control.

Samples for testing were transfected into 4 individual wells and firefly and Renilla Luciferase activities were determined 48 h post-transfection using the Dual-Luciferase Assay System (Promega) and a Synergy™ 2 Luminescence microplate reader (Biotek) according to the respective manufacturer's protocol. The firefly/Renilla activity ratios were determined for each well, and the inhibition efficiency of siRNA or shRNAs were calculated by normalizing to respective controls.

Results

The graphs in FIGS. 10A and B show luciferase activities (+/−SD; n=4) in cells transfected with varying quantities of chemically synthesised siRNA23 (A) or shRNA23 expression constructs (B) targeting pGL3-23 using the conditions listed in Tables 5 and 6. Even at the lowest concentrations, the siRNA and shRNA based on SEQ ID NO:23 are downregulated relative to the negative control (siNC or shNC—arbitrarily set at 1). The positive control luciferase siRNA and shRNA also downregulated luciferase expression levels from pGL3-23.

Example 8: Assaying the Effectiveness of ddRNAi Agents In Vivo

Mouse models for HBV are available, such as HBV infected NOD/SCID mice (Yang et al. 2002; Ketzinel-Gilad et al. 2006), as well as transgenic mouse lines expressing HBV, either or both of which could be used for these experiments.

Injection of ddRNAi agents into mouse tail veins will be used to deliver the agents to the liver. Inhibition of HBV replication can be monitored at various time points using qRT-PCR assays to determine the levels of HBV pol mRNA in liver tissues or by quantifying levels of circulating HBsAg and HBeAg in animals treated with ddRNAi agents of the invention compared to appropriate control animals such as mice injected with scrambled sequences or irrelevant DNAs, as described above.

Suitable expression constructs for stable expression of the ddRNAi agents include lentiviral vectors.

Example 9: In Vivo Testing of the Pre-Clinical Candidate in a Normal Mouse Model One delivery system envisaged in vivo testing of the pre-clinical candidate in a normal mouse model is AAV. For AAV, the ddRNAi constructs will be packaged in vitro using strategies well known to those familiar with the art and injected intravenously into HBV infected NOD/SCID mice and/or HBV transgenic mice. Inhibition of HBV replication will be monitored as described above.

It will be understood that the invention disclosed and defined in this specification extends to all alternative combinations of two or more of the individual features mentioned or evident from the text or drawings. All of these different combinations constitute various alternative aspects of the invention.

What is claimed is:

1. A DNA-directed RNA interference (ddRNAi) agent for inhibiting expression of one or more target sequences in one or more Hepatitis B virus (HBV) genes, the ddRNAi agent comprising:
   a first effector sequence of at least 17 nucleotides in length;
   a second effector sequence of at least 17 nucleotides in length;
   a second effector complement sequence; and
   a first effector complement sequence;
   wherein each effector sequence is substantially complementary to a predicted transcript of one of the target sequences, and wherein one of the first and second effector sequences comprises a nucleotide sequence consisting of any 10 or more contiguous nucleotides within the sequence set forth in SEQ ID NO: 9.

2. A ddRNAi agent according to claim 1, comprising a third effector sequence of at least 17 nucleotides in length and a third effector complement sequence.

3. A ddRNAi agent according to claim 1 comprising, in a 5' to 3' direction:

the first effector sequence of at least 17 nucleotides in length;
the first effector complement sequence;
the second effector sequence of at least 17 nucleotides in length; and
the second effector complement sequence.

4. A ddRNAi agent according to claim 2 comprising in a 5' to 3' direction:
the first effector sequence of at least 17 nucleotides in length;
the first effector complement sequence;
the second effector sequence of at least 17 nucleotides in length;
the second effector complement sequence;
the third effector sequence of at least 17 nucleotides in length; and
the third effector complement sequence.

5. A ddRNAi agent according to claim 1, wherein:
one of the first and second effector sequences comprises a nucleotide sequence consisting of any 10 or more contiguous nucleotides within the sequence set forth in SEQ ID NO: 9; and
the other effector sequence comprises a nucleotide sequence consisting of any 10 or more contiguous nucleotides within a sequence selected from the sequences set forth in SEQ ID NOs: 1 to 8 and 10 to 27.

6. A ddRNAi agent according to claim 5, wherein:
one of the first and second effector sequences comprises a nucleotide sequence consisting of any 10 or more contiguous nucleotides within the sequence set forth in SEQ ID NO: 9; and
the other effector sequence comprises a nucleotide sequence consisting of any 10 or more contiguous nucleotides within a sequence selected from the sequences set forth in SEQ ID NOs: 3, 12, 13 and 23.

7. A ddRNAi expression cassette for expressing a ddRNAi agent according to claim 1, the expression cassette comprising:
one or more promoter sequences;
one or more DNA sequences that encode for one or more effector sequences;
one or more DNA sequences that encode for one or more effector complement sequences; and one or more terminator sequences;
and optionally:
one or more DNA sequences that encode for loop sequences; and/or
one or more enhancer sequences.

8. A ddRNAi expression cassette according to claim 7, wherein the one or more DNA sequences that encode for one or more effector sequences comprises:
a DNA sequence encoding for an effector sequence comprising a nucleotide sequence consisting of any 10 or more contiguous nucleotides within the sequence set forth in SEQ ID NO: 9; and
one or more DNA sequences that encode for one or more effector sequences, each comprising 10 or more contiguous nucleotides within a sequence set forth in any one of SEQ ID NOs: 1 to 8 or 10 to 27.

9. A ddRNAi expression construct comprising a ddRNAi expression cassette according to claim 7.

10. A method of treating acute or chronic HBV infection in a subject comprising administering a therapeutically effective amount of a ddRNAi agent according to claim 1 to thereby treat the acute or chronic HBV infection in the subject.

11. A method of reducing HBV viral load in a subject comprising administering a therapeutically effective amount of a ddRNAi agent according to claim 1 to thereby reduce HBV viral load in the subject.

12. A method of reducing the severity of symptoms associated with HBV infection in a subject comprising administering a therapeutically effective amount of a ddRNAi agent according to claim 1 to thereby reduce the severity of symptoms associated with HBV infection in the subject.

13. A method of reducing the infectivity of HBV comprising administering a therapeutically effective amount of a ddRNAi agent according to claim 1 to thereby reduce infectivity of HBV.

14. A method according to claim 10, wherein the ddRNAi agent inhibits expression of at least the HBV polymerase gene to thereby treat the acute or chronic HBV infection in the subject.

15. A pharmaceutical composition comprising a ddRNAi agent according to claim 1 and a pharmaceutically acceptable carrier or diluent.

16. A method of treating acute or chronic HBV infection in a subject comprising administering a therapeutically effective amount of a ddRNAi expression construct of claim 9 to thereby treat the acute or chronic HBV infection in the subject.

17. A method of reducing HBV viral load in a subject comprising administering a therapeutically effective amount of a ddRNAi expression construct of claim 9 to thereby reduce HBV viral load in the subject.

18. A method of reducing the severity of symptoms associated with HBV infection in a subject comprising administering a therapeutically effective amount of a ddRNAi expression construct of claim 9 to thereby reduce the severity of symptoms associated with HBV infection in the subject.

19. A method of reducing the infectivity of HBV comprising administering a therapeutically effective amount of a ddRNAi expression construct of claim 9 to thereby reduce infectivity of HBV.

20. A pharmaceutical composition comprising a ddRNAi expression construct according to claim 9 and a pharmaceutically acceptable carrier or diluent.

21. The ddRNAi agent according to claim 1, wherein one of the first and second effector sequences comprises a nucleotide sequence consisting of any 15 or more contiguous nucleotides within the sequence set forth in SEQ ID NO: 9.

22. The ddRNAi agent according to claim 1, wherein one of the first and second effector sequences comprises a nucleotide sequence consisting of any 16 or more contiguous nucleotides within the sequence set forth in SEQ ID NO: 9.

23. The ddRNAi agent according to claim 1, wherein one of the first and second effector sequences comprises a nucleotide sequence consisting of any 17 or more contiguous nucleotides within the sequence set forth in SEQ ID NO: 9.

24. The ddRNAi agent according to claim 1, wherein one of the first and second effector sequences comprises a nucleotide sequence consisting of any 18 or more contiguous nucleotides within the sequence set forth in SEQ ID NO: 9.

25. The ddRNAi agent according to claim 1, wherein one of the first and second effector sequences comprises a nucleotide sequence consisting of any 19 or more contiguous nucleotides within the sequence set forth in SEQ ID NO: 9.

26. The ddRNAi agent according to claim 1, wherein one of the first and second effector sequences comprises a nucleotide sequence consisting of any 20 contiguous nucleotides within the sequence set forth in SEQ ID NO: 9.

* * * * *

SEQUENCE LISTING

```
<160> NUMBER OF SEQ ID NOS: 19

<210> SEQ ID NO 1
<211> LENGTH: 18
<212> TYPE: RNA
<213> ORGANISM: Hepatitis B virus

<400> SEQUENCE: 1
gauugacgau aagggaga                                               18

<210> SEQ ID NO 2
<211> LENGTH: 19
<212> TYPE: RNA
<213> ORGANISM: Hepatitis B virus

<400> SEQUENCE: 2
uugaagaccc aaucuggau                                              19

<210> SEQ ID NO 3
<211> LENGTH: 23
<212> TYPE: RNA
<213> ORGANISM: Hepatitis B virus

<400> SEQUENCE: 3
gccgggcaac gggguaaagg uuc                                         23

<210> SEQ ID NO 4
<211> LENGTH: 29
<212> TYPE: RNA
<213> ORGANISM: Hepatitis B virus

<400> SEQUENCE: 4
uauuugcggg agaggacaac agaguuauc                                   29

<210> SEQ ID NO 5
<211> LENGTH: 23
<212> TYPE: RNA
<213> ORGANISM: Hepatitis B virus
```

```
<400> SEQUENCE: 5
uccugaugug auguucucca ugu                                          23

<210> SEQ ID NO 6
<211> LENGTH: 20
<212> TYPE: RNA
<213> ORGANISM: Hepatitis B virus

<400> SEQUENCE: 6
aaggccuccg ugcggugggg                                              20

<210> SEQ ID NO 7
<211> LENGTH: 22
<212> TYPE: RNA
<213> ORGANISM: Hepatitis B virus

<400> SEQUENCE: 7
gguauuguuu acacagaaag gc                                           22

<210> SEQ ID NO 8
<211> LENGTH: 19
<212> TYPE: RNA
<213> ORGANISM: Hepatitis B virus

<400> SEQUENCE: 8
gauguguucu uguggcaag                                               19

<210> SEQ ID NO 9
<211> LENGTH: 21
<212> TYPE: RNA
<213> ORGANISM: Hepatitis B virus

<400> SEQUENCE: 9
gggaaagccc uacgaaccac u                                            21

<210> SEQ ID NO 10
<211> LENGTH: 20
<212> TYPE: RNA
<213> ORGANISM: Hepatitis B virus

<400> SEQUENCE: 10
guggagacag cggguaggc                                               20

<210> SEQ ID NO 11
<211> LENGTH: 18
<212> TYPE: RNA
<213> ORGANISM: Hepatitis B virus

<400> SEQUENCE: 11
gaggacaaca gaguuauc                                                18

<210> SEQ ID NO 12
<211> LENGTH: 23
<212> TYPE: RNA
<213> ORGANISM: Hepatitis B virus

<400> SEQUENCE: 12
gcccacuccc auaggaauuu ucc                                          23

<210> SEQ ID NO 13
<211> LENGTH: 18
<212> TYPE: RNA
<213> ORGANISM: Hepatitis B virus
```

```
<400> SEQUENCE: 13
ggaucuugca gaguuugg                                                    18

<210> SEQ ID NO 14
<211> LENGTH: 20
<212> TYPE: RNA
<213> ORGANISM: Hepatitis B virus

<400> SEQUENCE: 14
cguugccggg caacggggua                                                  20

<210> SEQ ID NO 15
<211> LENGTH: 23
<212> TYPE: RNA
<213> ORGANISM: Hepatitis B virus

<400> SEQUENCE: 15 gcaauuccg uccgaagguu ugg                                               23

<210> SEQ ID NO 16
<211> LENGTH: 20
<212> TYPE: RNA
<213> ORGANISM: Hepatitis B virus

<400> SEQUENCE: 16
guuggaggac aggagguugg                                                  20

<210> SEQ ID NO 17
<211> LENGTH: 22
<212> TYPE: RNA
<213> ORGANISM: Hepatitis B virus

<400> SEQUENCE: 17
guuggaggac aggagguugg ug                                               22

<210> SEQ ID NO 18
<211> LENGTH: 22
<212> TYPE: RNA
<213> ORGANISM: Hepatitis B virus

<400> SEQUENCE: 18
gaagugcaca cgguccggca ga                                               22

<210> SEQ ID NO 19
<211> LENGTH: 22
<212> TYPE: RNA
<213> ORGANISM: Hepatitis B virus

<400> SEQUENCE: 19
caagaugcug uacagacuug gc                                               22
```